(12) United States Patent
Dharmakumar et al.

(10) Patent No.: US 11,445,912 B2
(45) Date of Patent: Sep. 20, 2022

(54) ROBUST MYOCARDIAL BLOOD OXYGEN LEVEL DEPENDENT MAGNETIC RESONANCE IMAGING WITH LONG ACTING CORONARY VASODILATORS

(71) Applicant: Cedars-Sinai Medical Center, Los Angeles, CA (US)

(72) Inventors: Rohan Dharmakumar, Moorpark, CA (US); Hsin-Jung Yang, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 362 days.

(21) Appl. No.: 15/763,669

(22) PCT Filed: Sep. 30, 2016

(86) PCT No.: PCT/US2016/054890
§ 371 (c)(1),
(2) Date: Mar. 27, 2018

(87) PCT Pub. No.: WO2017/059302
PCT Pub. Date: Apr. 6, 2017

(65) Prior Publication Data
US 2018/0271375 A1 Sep. 27, 2018

Related U.S. Application Data

(60) Provisional application No. 62/235,441, filed on Sep. 30, 2015.

(51) Int. Cl.
*A61B 5/00* (2006.01)
*G01R 33/50* (2006.01)
(Continued)

(52) U.S. Cl.
CPC ........ *A61B 5/0044* (2013.01); *A61B 5/02007* (2013.01); *A61B 5/055* (2013.01);
(Continued)

(58) Field of Classification Search
CPC .............. A61B 5/0044; A61B 5/02007; A61B 5/055; A61B 5/7207; A61B 6/03; A61B 6/503;
(Continued)

(56) References Cited

U.S. PATENT DOCUMENTS

2003/0065258 A1* 4/2003 Gupta ................. A61B 5/0555
600/410
2006/0210478 A1 9/2006 Weisskoff
(Continued)

FOREIGN PATENT DOCUMENTS

CA 3092698 A1 10/2019
EP 2916133 A1 9/2015
(Continued)

OTHER PUBLICATIONS

Carneiro, "MRI Relaxometry: Methods and Applications", Mar. 2006 (Year: 2006).*
(Continued)

*Primary Examiner* — Amanda Lauritzen Moher
*Assistant Examiner* — Brooke Lyn Klein
(74) *Attorney, Agent, or Firm* — Nixon Peabody LLP; Linda B. Huber; Suwei Zhu

(57) ABSTRACT

The invention provides various methods for imaging a subject's cardiovascular system. The imaging method may be used to provide a diagnosis or prognosis of various cardiovascular diseases in the subject, without contrast agents or radioactive tracers, and further generating a Gaussian Mixture Model to obtain a reference value of a normal myocardium.

32 Claims, 15 Drawing Sheets

(51) Int. Cl.
| | |
|---|---|
| A61B 6/03 | (2006.01) |
| G01R 33/56 | (2006.01) |
| A61B 5/02 | (2006.01) |
| A61B 5/055 | (2006.01) |
| A61B 6/00 | (2006.01) |
| G01R 33/48 | (2006.01) |
| A61B 5/145 | (2006.01) |

(52) U.S. Cl.
CPC ............. *A61B 5/7207* (2013.01); *A61B 6/03* (2013.01); *A61B 6/503* (2013.01); *G01R 33/481* (2013.01); *G01R 33/50* (2013.01); *G01R 33/5601* (2013.01); *A61B 5/14542* (2013.01); *A61B 6/037* (2013.01)

(58) Field of Classification Search
CPC .................. G01R 33/481; G01R 33/50; G01R 33/5601
See application file for complete search history.

(56) References Cited

U.S. PATENT DOCUMENTS

| | | | |
|---|---|---|---|
| 2006/0239920 A1 | 10/2006 | Kucharczyk et al. | |
| 2008/0267861 A1 | 10/2008 | Lieu et al. | |
| 2009/0161938 A1* | 6/2009 | Shekhar | A61B 8/483 382/131 |
| 2009/0259121 A1 | 10/2009 | Simonetti et al. | |
| 2009/0299436 A1* | 12/2009 | Mushahwar | A61N 1/36003 607/48 |
| 2011/0076255 A1* | 3/2011 | Pecora | C12N 5/0647 424/93.7 |
| 2012/0189538 A1 | 7/2012 | Gordi et al. | |
| 2013/0289397 A1 | 10/2013 | Bienenstock | |
| 2014/0088406 A1 | 3/2014 | Dharmakumar et al. | |
| 2014/0121511 A1 | 5/2014 | Kadrmas et al. | |
| 2014/0170069 A1 | 6/2014 | Dharmakumar et al. | |
| 2014/0257083 A1 | 9/2014 | McVeigh et al. | |
| 2015/0196207 A1* | 7/2015 | Friedrich | A61B 6/5288 600/443 |
| 2015/0230762 A1 | 8/2015 | Alpert et al. | |
| 2016/0104279 A1 | 4/2016 | Li et al. | |
| 2017/0340266 A1 | 11/2017 | Gardner et al. | |
| 2018/0185519 A1 | 7/2018 | Dharmakumar et al. | |
| 2019/0038781 A1 | 2/2019 | Dharmakumar et al. | |
| 2021/0022640 A1 | 1/2021 | Dharmakumar et al. | |

FOREIGN PATENT DOCUMENTS

| | | |
|---|---|---|
| EP | 3784118 A1 | 3/2021 |
| JP | 2021521966 A | 8/2021 |
| WO | 2012/151583 A1 | 11/2012 |
| WO | 2013041834 A1 | 3/2013 |
| WO | 20150123598 A1 | 8/2015 |
| WO | 2017059302 A1 | 4/2017 |
| WO | 2019/210145 A1 | 10/2019 |
| WO | 2020/163783 A1 | 8/2020 |

OTHER PUBLICATIONS

Gao, "Highly automatic quantification of myocardial oedema in patients with acute myocardial infarction using bright blood T2-weighted CMR", 2013 (Year: 2013).*
International Search Report and Written Opinion for PCT/US2020/17320, dated Jun. 10, 2020.
Doneva et al., Compressed Senseing Reconstruction for Magnetic Resonance Parameter Mapping, Magnetic Resonance in Medicine, 2010, vol. 64, pp. 1114-1120.
Pang et al., Accelerated Whole-Heart Coronary MRA Using Motion-Corrected Sensitivity Encoding with Three-Dimensional Projection Reconstruction, Magnetic Resonance in Medicine, 2015, vol. 73, pp. 284-291.
Prieto, C., Undersampled Reconstruction Techniques to Speec up MRI, UCL PET-MRI Methodology Symposium, 2016, Division of Imaging Sciences and Biomedical Engineering King's College London, pp. 1-41.
Wright et al., Non-Cartesian Parallel Imaging Reconstruction, Journal of Magnetic Resonance Imagine, 2014, vol. 40, pp. 1022-1040.
Yang et al., Assessment of Myocardial Reactivity to Controlled Hypercapnia with Free-Breathing T2-Prepared Cardiac Blood Oxygen Level-Dependent MR Imaging, Radiology, 2014, vol. 272(2), pp. 397-406.
Yang et al., Free-Breathing, Motion-Corrected, Highly Efficient Whole Heart T2 Mapping at 3T with Hybrid Radial-Cartesian Trajectory, Magnetic Resonance in Medicine, 2016, vol. 75, pp. 126-136.
Yang et al., Arterial CO2 as a Potent Coronary Vasodilator: A Preclinical PET/MR Validation Study with Implication for Cardiac Stress Testing, J Nucl Med, 2017, vol. 58, pp. 953-960.
Yang et al., Accurate Needle-Free Assessment of Myocardial Oxygenation for Ischemic Heart Disease in Canines Using Magnetic Resonance Imaging, Sci Transl. Med, 2019, vol. 11, pp. 1-10.
International Preliminary Report on Patentability for PCT/US2016/054890 dated Apr. 12, 2018, 12 pages.
International Search Report and Written Opinion for PCT/US2016/54890 dated Feb. 3, 2017, 23 pages.
Vohringer et al., Oxygenation-sensitive CMR for assessing vasodilator-induced changes of myocardial oxygenation. Journal of Cardiovascular Magnetic Resonance, 2010, retrieved from: "https://www.ncbi.nlm.nih.gov/pmc/articles/PMC2861023/pdf/1532-429X-12-20.pdf" on Jan. 10, 2017, 7 pages.
Seemann, Improvements to Quantification Algorithms for Myocardial Infarction in CMR Images, 2013, retrieved from: "http://lup.lub.lu.se/luur/download?func=downloadFile&recordOld=4128314&fileOld=4128321" on Jan. 10, 2017, 55 pages.
Chaddad, Automated Feature Extraction in Brain Tumor by Magnetic Resonance Imaging Using Gaussian Mixture Models, International Journal of Biomedical Imaging, 2015, retrieved from: "https://www.ncbi.nlm.nih.gov/pmc/articles/PMC4469084/pdf/IJBI2015-868031.pdf" on Jan. 10, 2017, 11 pages.
Kober et al., Myocardial arterial spin labeling, Journal of Cardiovascular Magnetic Resonance, 2016, 18:22, pp. 1-16.
Arnold et al., Myocardial Oxygenation in Coronary Artery Disease: In sights From Blood Oxygen Level-Dependent Magnetic Resonance Imaging at 3 Tesla, Journal of the American College of Cardiology, 2012, 59:22, pp. 1954-1964.
Parnham et al., Impaired Myocardial Oxygenation Response to Stress in Patients With Chronic Kidney Disease, J. Am. Heart. Assoc. 2015, 4(8), e002249, 12 pages.
Karamitsos et al., Relationship Between Regional Myocardial Oxygenation and Perfusion in Patients With Coronary Artery Disease: Insights From Cardiovascular Magnetic Resonance and Positron Emission Tomography, Circ. Cardiovasc. Imaging, 2010, 3:1, pp. 32-40.
Tsaftaris et al., Ischemic Extent as a Biomarker for Characterizing Severity of Coronary Artery Stenosis With Blood Oxygen-Sensitive MRI, J. Magn. Reson. Imaging, 2012, 35, pp. 1338-1348.
Al Jaroudi et al., Regadenoson: A New Myocardial Stress Agent, J. Am. Coll. Cardiol., 2009, 54(13), pp. 1123-1130.
Gabizon et al., Liposomes as in Vivo Carriers of Adriamycin: Reduced Cardiac Uptake and Preserved Antitumor Activity in Mice, Cancer Research, 1982, 42, pp. 4734-4739.
Yang et al., Towards reliable myocardial blood-oxygen-level-dependent (BOLD) CMR using late effects of regadenoson with simultaneous 13n-ammonia pet validation in a whole-body hybrid PET/MR system, Journal of Cardiovascular Magnetic Resonance, 2016, 18 (Suppl 1): O19, 3 pages.
Giri et al., T2 quantification for improved detection of myocarial edema, Journal of Cardiovascular Magnetic Resonance, 2009, 11:56, pp. 1-13.
Jaroudi et al., Expression profiling of DNA repair genes in human ooxytes and blastocysts using microarrays, Human Reproduction, 2009, 24(10), pp. 2649-2655.
Felmlee et al., Mechanism-Based Pharmacodynamic Modeling, Methods Mol Biol. 2012, 929, pp. 583-600.

(56) References Cited

OTHER PUBLICATIONS

Wang et al. Color image segmentation using pixel wise support vector machine classification, Pattern Recognition, 2011, 44(4), pp. 777-787.
Zoghbi et al., Selective adenosine agonists and myocardial perfusion imaging. J.Nucl.Cardiol., 2012, 19(1), pp. 126-141.
Avants et al., A reproducible evaluation of ANTs similarity metric performance in brain image registration, Neuroimage, 2011, 54, pp. 2033-2044.
Gordi et al., A population pharmacokinetic/pharmacodynamic analysis of regadenoson, an adenosine A2A-receptor agonist, in healthy male volunteers, Clinical pharmacokinetics, 2006, 45, pp. 1201-1212.
International Search Report and Written Opinion for PCT/US2019/29316 dated Jul. 15, 2019, 11 pages.
International Preliminary Report on Patentability for PCT/US2019/29316 dated Oct. 27, 2020, 8 pages.
Miller, D, Impact of Selective Adenosine A2A Receptor Agonists on Cardiac Imaging, Journal of American College of Cardiology, 2005, vol. 46(11), pp. 2076-2078.
Yang et al., Beat-by-Beat Dynamic Assessment of Myocardial Oxygenation with Highly Time-Resolved, Free-breathing, Ungated Cardiac T2 BOLD MRI Using a Low-Rank Tensor Formulation, Joint Annual Meeting ISMRM-ESMRMB, 2018, Abstract Only.
Supplementary European Search Report for EP 19792195 dated Dec. 8, 2021, 8 pages.
Li et al., Myocardial Signal Respone to Dipyridamole and Dobutamine: Demonstration of the Bold Effect Using a Double-Echo Gradient-Echo Sequence, Magnetic Resonance in Medicine, 1996, vol. 36(1), pp. 16-20.
Stalder et al., Robust Cardiac Bold MRI Using an fMRI-Like Approach with Repeated Stress Paradigms, Magnetic Resonance in Medicine, 2015, vol. 73, pp. 577-585.
Hsin-Jung Yang, Oral presentation at 19th Annual Scientific Sessions of Society for Cardiovascular Magnetic Resonance (SCMR), "Towards Reliable Myocardial Blood-Oxygen-Level-Dependent (BOLD) CMR Using Late Effects of Regadenoson with Simultaneous 13N-ammonia PET Validation in a Whole-body Hybrid PET/MR System", Jan. 29, 2016.
Proceedings from the 20th annual SCMR Scientific Sessions, Feb. 1-4, 2017, Abstract Supplement.

\* cited by examiner

*FIG. 9*
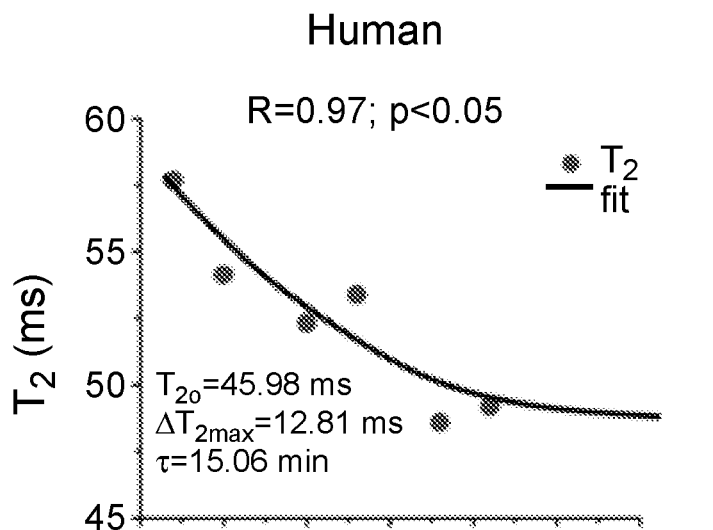
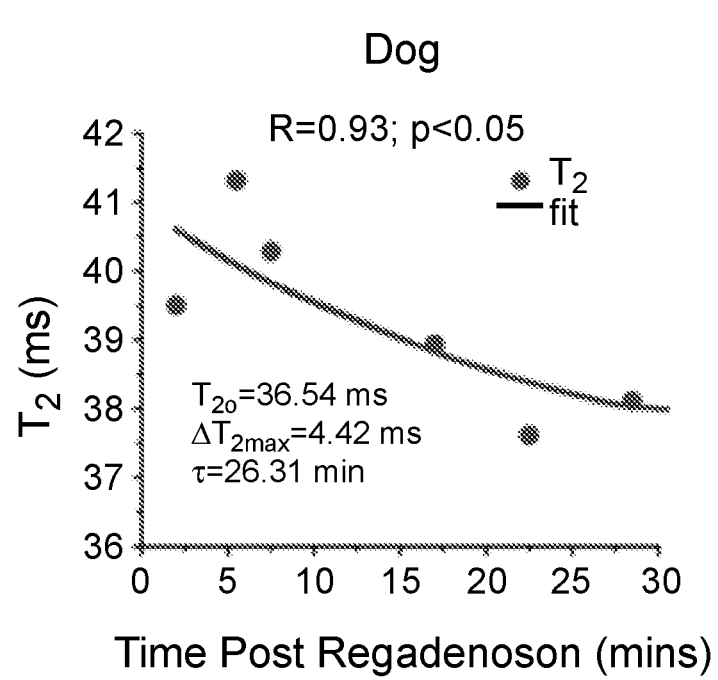

$T_2(t) + T_{2o} + \Delta T_{2max}(\text{Exp}(-t/\tau))$

LGE MRI

Affected

Remote

N$^{13}$ PET Perfusion

MBR$_{CRM}$

CNR$_{CRM}$=4.58

MBR$_{con}$

CNR$_{con}$=1.84

ROBUST MYOCARDIAL BLOOD OXYGEN LEVEL DEPENDENT MAGNETIC RESONANCE IMAGING WITH LONG ACTING CORONARY VASODILATORS

CROSS-REFERENCE TO RELATED APPLICATIONS

This application is a National Phase of International Application No. PCT/US2016/054890, filed Sep. 30, 2016, which designated the U.S. and that International Application was published under PCT Article 21(2) in English. This application claims priority under 35 U.S.C. § 119(e) to U.S. Provisional Application No. 62/235,441, filed Sep. 30, 2015, the contents of which are herein incorporated by reference in their entirety.

STATEMENT REGARDING FEDERALLY SPONSORED RESEARCH OR DEVELOPMENT

This invention was made with government support under Grant No. HL091989 awarded by National Institutes of Health. The government has certain rights in the invention.

FIELD OF THE INVENTION

The invention relates to cardiovascular imaging, particularly cardiovascular imaging under cardiac stress test for diagnosing and/or prognosing various cardiovascular diseases.

BACKGROUND

All publications cited herein are incorporated by reference in their entirety to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Ischemic Heart Disease (IHD) leads to narrowing of the small blood vessels that supply blood and oxygen to the heart. Typically, atherosclerosis is the cause of IHD. As the coronary arteries narrow, blood flow to the heart can slow down or stop, causing, amongst other symptoms, chest pain (stable angina), shortness of breath and myocardial infarction. Numerous tests help diagnose IHD. Such tests include coronary angiography/arteriography, CT angiography, echocardiogram, electrocardiogram (ECG), electron-beam computed tomography (EBCT), magnetic resonance angiography, nuclear scan and exercise stress test. Functional assessment of the myocardium (for example the assessment of myocardium's oxygen status) requires that a patient's heart is stressed either via controlled exercise or pharmacologically.

Assessment of vascular reactivity in the heart is the hallmark of stress testing in cardiac imaging aimed at understanding ischemic heart disease. This is routinely done in nuclear medicine with radionuclide injection (such as Thallium) in conjunction with exercise to identify territories of the heart muscle that are subtended by a suspected narrowed coronary artery. In patients who are contraindicated for exercise stress-testing, this approach is typically used in conjunction with hyperemia inducing drugs, for example via adenosine infusion. Coronary narrowing is expected to reduce hyperemic response and the perfusion reserve. Since nuclear methods are hampered by the need for radioactive tracers combined with limited imaging resolution, other imaging methods, such as ultrasound (using adenosine along with microbubble contrast) and MRI (also using adenosine and various conjugates of gadolinium (Gd) (first-pass perfusion) or alterations in oxygen saturation in response to hyperemia, also known as the Blood-Oxygen-Level-Dependent (BOLD) effect) are under clinical investigation. Nonetheless, in patients who are contraindicated for exercise stress-testing, currently all imaging approaches require adenosine to elicit hyperemia. However, adenosine has undesirable side effects (such as the feeling of "impending doom", bradycardia, arrhythmia, transient or prolonged episode of asystole, ventricular fibrillation (rarely), chest pain, headache, dyspnea, and nausea), making it less than favorable for initial or follow-up studies and many patients request that they do not undergo repeated adenosine stress testing. However, repeated stress testing is indicated in a significant patient population to assess the effectiveness of interventional or medical therapeutic regimens.

Cardiac imaging (e.g., MM, ECG, PET and SPECT) is an important diagnostic and prognostic medical tool. Depending on the imaging modality (e.g., MRI, ECG, PET, and SPECT) one can gain valuable information about the structure of the heart, its functionality, and its metabolism. While cardiac imaging is often assessed under resting conditions, the way the heart responds to physiological stress can provide important insight into its overall function and metabolic status. Various "stress tests" exist, including pharmacological agents and physical stress (i.e., exercise), which aim to make the heart work harder (i.e., increase metabolic demand). In conditions in which oxygen delivery is compromised, increasing myocardial work causes a mismatch between oxygen delivery and oxygen demand, leading to a functional deficit.

Exercise is used as a stress test, and it closely reflects activities of daily living, but is often confounded by respiratory and movement artifact (and thus negatively influences interpretation of results). Moreover, exercise is not feasible in more than 50% of cases, because they cannot exercise to a level where derangements can accurately be assessed.

Another available stress test is infusion of pharmacological agents which simulate exercise (e.g., dobutamine) by increasing myocardial oxygen demand through increases in heart rate and contractility, and arterial blood pressure. Dobutamine is however a non-specific beta-adrenergic agonist, which in addition to increasing heart rate, cardiac contractility, and blood pressure could also be causing beta-adrenergic vasodilation (via coronary beta receptors), and thus is non-specific. Also, vasodilating drugs (e.g., adenosine, regadenoson, and acetylcholine) may be infused either directly into the coronary arteries, or systemically into a peripheral vein, to assess coronary perfusion reserve. This test is very specific for the vasodilating drug being used however, and is often associated with severe patient discomfort and even death. Accordingly, there is a need in the art for cardiovascular imaging methods which are precise, easily reproducible, do not have side-effects of existing methods, and improve patient comfort.

SUMMARY OF THE INVENTION

The following embodiments and aspects thereof are described and illustrated in conjunction with compositions and methods which are meant to be exemplary and illustrative, not limiting in scope.

Myocardial BOLD MRI approach has undergone significant improvement over the past two decades. This approach overcomes existing limitations of ionizing radiations or exogenous contrast media associated with existing methods which aim to image regions of the heart muscle that are inadequately perfused especially under conditions of physiological demands. While BOLD MM approach has been introduced into the research arena, even the state-of-the-art BOLD methods are plagued with significant image artifacts, especially during the infusion of pharmacological stress agents. This limitation has been the major obstacle for advancing cardiac BOLD MM into the clinical environment. Image quality improvements have been sought to overcome the artifacts. However, these efforts helped to improve the image quality at rest, no advancements have taken place for improving image artifacts during stress. The inventors have provided a new imaging approach that overcomes these artifacts, which would empower BOLD MM to accurately visualize the BOLD signal changes under stress.

Various embodiments of the present invention provide a method of imaging a subject's cardiovascular system. The method may consist of or may consist essentially of or may comprise: (a) imaging the subject's cardiovascular system at rest; (b) administering a vasodilator to the subject; and (c) imaging the subject's cardiovascular system after administering the vasodilator. In various embodiments, step (c) is performed about 5-6, 6-7, 7-8, 8-9, 9-10, 10-11, 11-12, 13-14, 14-15, 15-16, 16-17, 18-19, 19-20, 20-21, 21-22, 22-23, 23-24, or 24-25 minutes after step (b). In various embodiments, step (c) is performed about 10, 11, 12, 13, 14, or 15 minutes after step (b). In some embodiments, the method further comprises diagnosing the subject as having a cardiovascular disease. In some embodiments, the method further comprises prognosing the subject as being likely to develop or rapidly advance a cardiovascular disease. In some embodiments, the method further comprises prognosing the subject as having a higher probability of developing a cardiovascular disease as compared to a healthy subject. In various embodiments, the diagnosis and/or prognosis is based on the imaging results at rest and after administering the vasodilator. In some embodiments, the method further comprises administering a treatment of the cardiovascular disease to the subject, thereby treating the cardiovascular disease. In some embodiments, the subject is human. In some embodiments the vasodilator induces hyperemia. In some embodiments, the vasodilator is a selective $A_{2A}$ adenosine receptor agonist. In some embodiments, the selective $A_{2A}$ adenosine receptor agonist is regadenoson, or a functional equivalent, analog, derivative or salt. In some embodiments, the vasodilator is administered at about 0.01-0.02, 0.02-0.03, 0.03-0.04, 0.04-0.05, 0.05-0.06, 0.06-0.07, 0.07-0.08, 0.08-0.09, 0.09-0.1, 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 5-6, 6-7, 7-8, 8-9, or 9-10 mg, or a combination thereof. In some embodiments, the vasodilator is administered at about 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 5-6, 6-7, 7-8, 8-9, 9-10, 10-20, 20-30, 30-40, 40-50, 50-60, 60-70, 70-80, 80-90, or 90-100 µg/kg body weight, or a combination thereof. In some embodiments, the vasodilator is administered intravascularly, intravenously, intraarterially, or intracoronary. In some embodiments, the vasodilator is administered as a single bolus. In some embodiments, the single bolus comprises about 0.01-0.02, 0.02-0.03, 0.03-0.04, 0.04-0.05, 0.05-0.06, 0.06-0.07, 0.07-0.08, 0.08-0.09, 0.09-0.1, 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 5-6, 6-7, 7-8, 8-9, or 9-10 mg of the vasodilator. In some embodiments, imaging the subject's cardiovascular system comprises imaging the subject's heart. In some embodiments, imaging the subject's cardiovascular system comprises imaging the subject's coronary arteries. In some embodiments, imaging the subject's cardiovascular system comprises blood-oxygen-level dependent (BOLD) magnetic resonance imaging (MRI) of the subject's cardiovascular system. In some embodiments, imaging the subject's cardiovascular system comprises performing myocardial perfusion imaging (MPI). In some embodiments, MPI is performed using blood-oxygen-level dependent (BOLD) magnetic resonance imaging (MRI). In some embodiments, the method further comprises, calculating myocardial BOLD response. In some embodiments, no radioactive tracer or contrast agent is administered to the subject. In some embodiments, the method further comprises prognosing the subject as being likely to develop a cardiovascular disease.

In various embodiments, the present invention provides a blood oxygen level dependent (BOLD) magnetic resonance imaging (MM) method for obtaining one or more coronary dynamic parameters of a subject's cardiovascular system, comprising: (a) imaging the subject's cardiovascular system at rest to obtain a rest image; (b) administering an effective amount of a vasodilator to the subject, wherein the vasodilator has an extended vasodilatory state; (c) obtaining a series of images of the subject's cardiovascular system to obtain a plurality of stress images; (d) registering the stress images to the rest image to obtain a plurality of motion-corrected images; (e) applying the motion-corrected images to a first mathematical model; and (f) extracting the one or more coronary dynamic parameters from the first mathematical model. In some embodiments, the subject's cardiovascular system comprises the subject's heart. In some embodiments, the subject's cardiovascular system comprises the subject's coronary arteries. In some embodiments, the subject's cardiovascular system comprises the subject's myocardium. In some embodiments, the vasodilator is selected from regadenoson, binodenoson, apadenoson, and dipyridamole. In some embodiments, the vasodilator is regadenoson. In some embodiments, obtaining a series of images comprises imaging at a time interval. In some embodiments, the time interval is from about 1 minute to about 10 minutes between each image. In some embodiments, the time interval is from about 1 minute to about 5 minutes between each image. In some embodiments, the time interval is from about 5 minutes to about 10 minutes between each image. In some embodiments, the method further comprises applying the one or more coronary dynamic parameters to a second mathematical model to obtain a reference value, wherein a change in the one or more coronary dynamic parameters relative to the reference value is indicative of a cardiovascular disease in the subject's cardiovascular system. In some embodiments, the cardiovascular disease is selected from infarcted myocardium, coronary artery disease, coronary heart disease, ischemic heart disease, cardiomyopathy, stroke, hypertensive heart disease, heart failure, pulmonary heart disease, ischemic syndrome, coronary microvascular disease, cardiac dysrhythmias, rheumatic heart disease, aortic aneurysms, cardiomyopathy, atrial fibrillation, congenital heart disease, endocarditis, inflammatory heart disease, endocarditis, inflammatory cardiomegaly, myocarditis, valvular heart disease, cerebrovascular disease, and peripheral artery disease. In some embodiments, the cardiovascular disease is ischemic heart disease. In some embodiments, the cardiovascular disease is infarcted myocardium. In some embodiments, the first mathematical model is a mono-exponential model, wherein the mono-exponential model is: $T_2(t)=T_{2o}+\Delta T_{2max} \exp(-t/\tau)$, wherein $T_2$ is a transverse relaxation time, t is a time period following administration of the vasodilator to the subject, $T_{2o}$ is a baseline $T_2$, $\Delta T_{2max}$ is a maximum $T_2$ change from rest, and $\tau$ is a coronary relaxation time constant. In some embodiments, the coronary dynamic parameters are any one or more of $\tau$, $\Delta T_{2max}$, $T_{2o}$, or combinations thereof. In some embodiments, the coronary dynamic parameters are any one or more of $T_2$, t, $T_{2o}$, $\Delta T_{2max}$, $\tau$, $\Delta T_{2max}/T_{2o}$, $\Delta T_{2max}/\tau$, $(\tau \times \Delta T_{2max})$, $dT_2/dt$, or combinations thereof. In some embodiments, the vasodilator is administered intravascularly, intravenously, intraarterially, or intracoronary. In some embodiments, the vasodilator is administered as a single bolus. In some embodiments, no radioactive tracer or contrast agent is administered to the subject. In some embodiments, the second mathematical model is a Gaussian mixed model (GMM). In some embodiments, the reference value is obtained from the Gaussian mixed model (GMM) comprising: (a) obtaining a weighted sum of two component Gaussian densities by applying the one or more coronary dynamic parameters extracted from the first mathematical model to the equation: $p(x|\mu, \sigma) = \Sigma_i w_i g(x|\mu_i, \sigma_i)$, wherein p is a summed density, x is the one or more coronary dynamic parameters extracted from the first mathematical model, i is 1 or 2, and g is the component Gaussian densities determined from the equation: $g(x|\mu_i, \sigma_i) = 1/|\sigma_i|^{1/2} \exp\{-\frac{1}{2}(x-\mu_i)'\sigma_i^{-1}(x-\mu_i)\}$, wherein $\mu_i$ is a mean value, $\sigma_i$ is a covariance, and w is a mixture weights, wherein the mixture weights satisfy a constraint that $\Sigma_i w_i = 1$; and (b) defining the component Gaussian density with a larger mean value as the reference value, wherein the reference value is the distribution of a normal myocardium. In some embodiments, a value of less than mean minus 2 standard deviation (mean-2SD) for one or more coronary dynamic parameters relative to the reference value is indicative of a diseased myocardium. In some embodiments, pixels corresponding to the normal myocardium are identified as remote territories. In some embodiments, pixels corresponding to the diseased myocardium are identified as affected territories.

In various embodiments, the present invention provides a method for identifying a cardiovascular disease in a subject's cardiovascular system, comprising: (a) imaging the subject's cardiovascular system at rest to obtain a rest image; (b) administering an effective amount of a vasodilator to the subject, wherein the vasodilator has an extended vasodilatory state; (c) obtaining a series of images of the subject's cardiovascular system to obtain a plurality of stress images; (d) registering the stress images to the rest image to obtain a plurality of motion-corrected images; (e) applying the motion-corrected images to a first mathematical model; and (f) extracting one or more coronary dynamic parameters from the first mathematical model; and (g) applying the one or more coronary dynamic parameters to a second mathematical model to obtain a reference value, wherein a change in one or more coronary dynamic parameters relative to the reference value is indicative of the cardiovascular disease in the subject's cardiovascular system. In some embodiments, the cardiovascular disease is selected from infarcted myocardium, coronary artery disease, coronary heart disease, ischemic heart disease, cardiomyopathy, stroke, hypertensive heart disease, heart failure, pulmonary heart disease, ischemic syndrome, coronary microvascular disease, cardiac dysrhythmias, rheumatic heart disease, aortic aneurysms, cardiomyopathy, atrial fibrillation, congenital heart disease, endocarditis, inflammatory heart disease, endocarditis, inflammatory cardiomegaly, myocarditis, valvular heart disease, cerebrovascular disease, and peripheral artery disease. In some embodiments, the cardiovascular disease is ischemic heart disease. In some embodiments, the cardiovascular disease is infarcted myocardium. In some embodiments, the subject's cardiovascular system comprises the subject's heart. In some embodiments, the subject's cardiovascular system comprises the subject's coronary arteries. In some embodiments, the subject's cardiovascular system comprises the subject's myocardium. In some embodiments, imaging the subject's cardiovascular system comprises blood oxygen level dependent (BOLD) magnetic resonance imaging (MM). In some embodiments, the vasodilator is selected from regadenoson, binodenoson, apadenoson, and dipyridamole. In some embodiments, the vasodilator is regadenoson. In some embodiments, obtaining a series of images comprises imaging at a time interval. In some embodiments, the time interval is from about 1 minute to about 10 minutes between each image. In some embodiments, the time interval is from about 1 minute to about 5 minutes between each image. In some embodiments, the time interval is from about 5 minutes to about 10 minutes between each image. In some embodiments, the model is a mono-exponential model, wherein the mono-exponential model is: $T_2(t)=T_{2o}+\Delta T_{2max} \exp(-t/\tau)$, wherein $T_2$ is a transverse relaxation time, t is a time period following administration of the vasodilator to the subject, $T_{2o}$ is an estimate of baseline $T_2$, $\Delta T_{2max}$ is an estimate of maximum $T_2$ change from rest, and $\tau$ is an estimate of coronary relaxation time constant. In some embodiments, the coronary dynamic parameters are any one or more of $\tau$, $\Delta T_{2max}$, and $T_{2o}$. In some embodiments, the coronary dynamic parameters are any one or more of $T_2$, t, $T_{2o}$, $\Delta T_{2max}$, $\tau$, $\Delta T_{2max}/T_{2o}$, $\Delta T_{2max}/\tau$, $(\tau \times \Delta T_{2max})$, $dT_2/dt$, or combinations thereof. In some embodiments, the vasodilator is administered intravascularly, intravenously, intraarterially, or intracoronary. In some embodiments, the vasodilator is administered as a single bolus. In some embodiments, no radioactive tracer or contrast agent is administered to the subject.

In various embodiments, the present invention provides a method for screening a subject's cardiovascular system for a cardiovascular disease, comprising: (a) imaging the subject's cardiovascular system at rest to obtain a rest image; (b) administering an effective amount of a vasodilator to the subject, wherein the vasodilator has an extended vasodilatory state; (c) obtaining a series of images of the subject's cardiovascular system to obtain a plurality of stress images; (d) registering the stress images to the rest image to obtain a plurality of motion-corrected images; (e) applying the motion-corrected images to a first mathematical model; and (f) extracting one or more coronary dynamic parameters from the first mathematical model; and (g) applying the one or more coronary dynamic parameters to a second mathematical model to obtain a reference value, wherein a change in one or more coronary dynamic parameters relative to the reference value is indicative of the cardiovascular disease in the subject's cardiovascular system. In some embodiments, the cardiovascular disease is selected from infarcted myocardium, coronary artery disease, coronary heart disease, ischemic heart disease, cardiomyopathy, stroke, hypertensive heart disease, heart failure, pulmonary heart disease, ischemic syndrome, coronary microvascular disease, cardiac dysrhythmias, rheumatic heart disease, aortic aneurysms, cardiomyopathy, atrial fibrillation, congenital heart disease, endocarditis, inflammatory heart disease, endocarditis, inflammatory cardiomegaly, myocarditis, valvular heart disease, cerebrovascular disease, and peripheral artery disease. In some embodiments, the cardiovascular disease is ischemic heart disease. In some embodiments, the cardiovascular disease is infarcted myocardium. In some embodiments, the subject's cardiovascular system comprises the subject's heart. In some embodiments, the subject's cardiovascular system comprises the subject's coronary arteries. In some embodiments, the subject's cardiovascular system comprises the subject's myocardium. In some embodiments, imaging the subject's cardiovascular system comprises blood oxygen level dependent (BOLD) magnetic resonance imaging (MM). In some embodiments, the vasodilator is selected from regadenoson, binodenoson, apadenoson, and dipyridamole. In some embodiments, the vasodilator is regadenoson. In some embodiments, obtaining a series of images comprises imaging at a time interval. In some embodiments, the time interval is from about 1 minute to about 10 minutes between each image. In some embodiments, the time interval is from about 1 minute to about 5 minutes between each image. In some embodiments, the time interval is from about 5 minutes to about 10 minutes between each image. In some embodiments, the model is a mono-exponential model, wherein the mono-exponential model is: $T_2(t)=T_{2o}+\Delta T_{2max} \exp(-t/\tau)$, wherein $T_2$ is a transverse relaxation time, t is a time period following administration of the vasodilator to the subject, $T_{2o}$ is an estimate of baseline $T_2$, $\Delta T_{2max}$ is an estimate of maximum $T_2$ change from rest, and $\tau$ is an estimate of coronary relaxation time constant. In some embodiments, the coronary dynamic parameters are any one or more of $\tau$, $\Delta T_{2max}$, and $T_{2o}$. In some embodiments, the coronary dynamic parameters are any one or more of $T_2$, t, $T_{2o}$, $\Delta T_{2max}$, $\tau$, $\Delta T_{2max}/T_{2o}$, $\Delta T_{2max}/\tau$, $(\tau \times \Delta T_{2max})$, $dT_2/dt$, or combinations thereof. In some embodiments, the vasodilator is administered intravascularly, intravenously, intraarterially, or intracoronary. In some embodiments, the vasodilator is administered as a single bolus. In some embodiments, no radioactive tracer or contrast agent is administered to the subject.

In various embodiments, the present invention provides a method for treating a cardiovascular disease in a subject in need thereof, comprising: (a) identifying the cardiovascular disease in the subject by imaging the subject's cardiovascular system at rest to obtain a rest image, administering an effective amount of a vasodilator to the subject, wherein the vasodilator has an extended vasodilatory state, obtaining a series of images of the subject's cardiovascular system to obtain a plurality of stress images, registering the stress images to the rest image to obtain a plurality of motion-corrected images, applying the motion-corrected images to a first mathematical model, extracting one or more coronary dynamic parameters from the first mathematical model, and applying the one or more coronary dynamic parameters to a second mathematical model to obtain a reference value, wherein a change in one or more coronary dynamic parameters relative to the reference value is indicative of the cardiovascular disease in the subject's cardiovascular system; and (b) administering a therapeutic treatment to the subject so as to treat the cardiovascular disease. In some embodiments, the therapeutic treatment is any one or more of coronary revascularization through stenting, coronary bypass grafting, or medical therapy, or combinations thereof. In some embodiments, the cardiovascular disease is selected from infarcted myocardium, coronary artery disease, coronary heart disease, ischemic heart disease, cardiomyopathy, stroke, hypertensive heart disease, heart failure, pulmonary heart disease, ischemic syndrome, coronary microvascular disease, cardiac dysrhythmias, rheumatic heart disease, aortic aneurysms, cardiomyopathy, atrial fibrillation, congenital heart disease, endocarditis, inflammatory heart disease, endocarditis, inflammatory cardiomegaly, myocarditis, valvular heart disease, cerebrovascular disease, and peripheral artery disease. In some embodiments, the cardiovascular disease is ischemic heart disease. In some embodiments, the cardiovascular disease is infarcted myocardium.

BRIEF DESCRIPTION OF THE DRAWINGS

Exemplary embodiments are illustrated in referenced figures. It is intended that the embodiments and figures disclosed herein are to be considered illustrative rather than restrictive.

FIG. 2E).

FIG. 9 illustrates, in accordance with various embodiments of the invention, representative Coronary Dynamic Parameter (CDP) curves of a human volunteer and a healthy dog. High R values present the good representation from the CDP model.

FIG. 15A: 2 min, FIG. 15B: 5 min and FIG. 15C: 10 min are plotted in the scatter plots and compared with the conventional single time point $T_2$ values (FIG. 15D). The pixels are labeled as remote (black asterisk) and affected (unfilled triangle). Affected pixels identified by the averaged Support Vector Machines (SVMs) were displayed in the corresponding panel and labeled as affected. Lowest error rate and best accuracy on disease identification was achieved with the 5 min CDPs.

FIG. 16A shows a representative coronary relaxation curve and least-squares fitting based on repeated $T_2$ mapping following regadenoson injection; FIG. 16B shows the corresponding multi-fold increase in MBR from the CRM ($MBR_{CRM}$) compared to conventional MBR ($MBR_{con}$) estimation; and FIG. 16C shows the linear regression between CRM-based and conventional estimates of MBR. Note the slope of the regression curve is significantly larger than 1 highlighting the amplification in BOLD signal response uncovered by the CRM that is likely masked by unreliable signal estimates from conventional estimates.

FIG. 17A shows a representative Late Gadolinium Enhancement (LGE) image with an anterior wall chronic infarction; FIG. 17B shows a significantly reduced perfusion on $^{13}$N—NH$_3$ PET post regadenoson administration (p.r.a.) in the infarct territory; FIG. 17C shows the MBR map based on CRM; and FIG. 17D shows the MBR estimated using the conventional approach based on BOLD signal responses at baseline and 2 minutes p.r.a. Note the improved BOLD CMR delineation of the perfusion defect territory in FIG. 17C compared to FIG. 17D. The small white arrows identify a healthy (remote) region that is hypointense in the conventional MBR ($MBR_{con}$) and is recovered by $MBR_{CRM}$ from the increased Contrast-To-Noise Ratio (CNR).

DETAILED DESCRIPTION OF THE INVENTION

Figure 1:
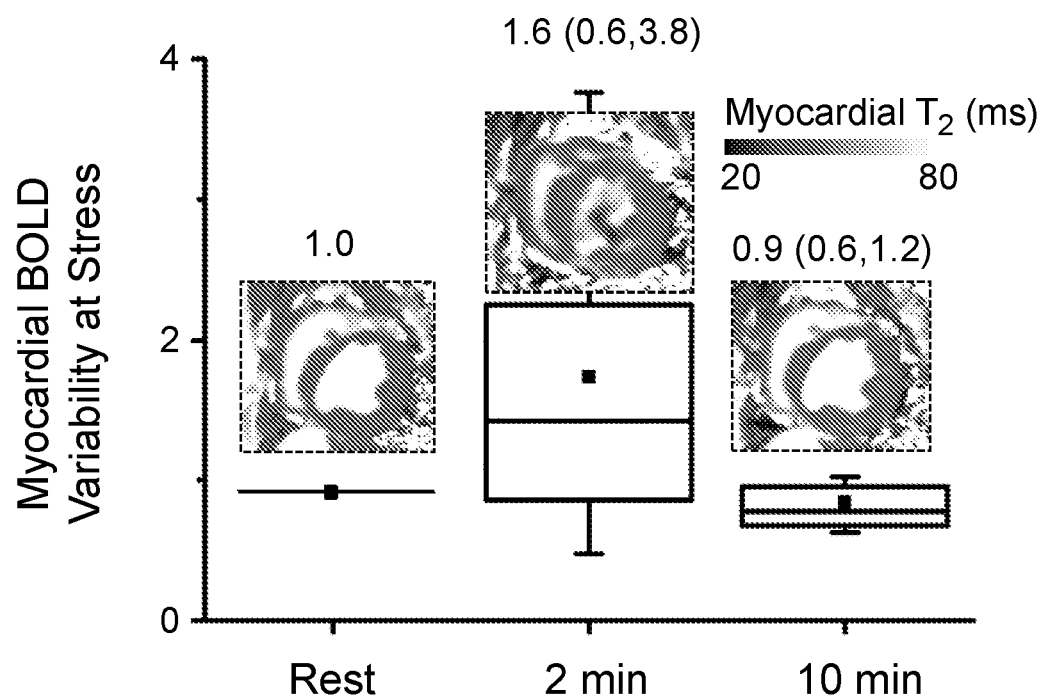
FIG. 1 illustrates, in accordance with various embodiments of the invention, myocardial BOLD variability at stress relative to rest. Box-plot of myocardial BOLD variability ($\sigma T_2$ (stress)/$\sigma T_2$ (rest)) computed from $T_2$ maps acquired at 2 min and 10 min post regadenoson administration (p.r.a) is shown. The mean and range of myocardial BOLD variability are shown under various conditions. Large myocardial BOLD variability is observed at 2 mins p.r.a. compared to rest and is markedly reduced at 10 mins p.r.a. Representative images acquired at the various conditions are shown for reference. Note the marked $T_2$ inhomogeneity in $T_2$ image at 2 min p.r.a. compared to rest and 10 min p.r.a. $\sigma T_2$ denotes the standard deviation of myocardial $T_2$.

All references cited herein are incorporated by reference in their entirety as though fully set forth. Unless defined otherwise, technical and scientific terms used herein have the same meaning as commonly understood by one of ordinary skill in the art to which this invention belongs. Allen et al., Remington: The Science and Practice of Pharmacy 22nd ed., Pharmaceutical Press (Sep. 15, 2012); Hornyak et al., Introduction to Nanoscience and Nanotechnology, CRC Press (2008); Singleton and Sainsbury, Dictionary of Microbiology and Molecular Biology 3rd ed., revised ed., J. Wiley & Sons (New York, N.Y. 2006); Smith, March's Advanced Organic Chemistry Reactions, Mechanisms and Structure 7th ed., J. Wiley & Sons (New York, N.Y. 2013); Singleton, Dictionary of DNA and Genome Technology 3rd ed., Wiley-Blackwell (Nov. 28, 2012); and Green and Sambrook, Molecular Cloning: A Laboratory Manual 4th ed., Cold Spring Harbor Laboratory Press (Cold Spring Harbor, N.Y. 2012), provide one skilled in the art with a general guide to many of the terms used in the present application.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. Unless otherwise defined, all technical and scientific terms used herein have the same meaning as commonly understood by one of ordinary skill in the art to which this invention belongs. It should be understood that this invention is not limited to the particular methodology, protocols, and reagents, etc., described herein and as such can vary. The definitions and terminology used herein are provided to aid in describing particular embodiments, and are not intended to limit the claimed invention, because the scope of the invention is limited only by the claims.

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

As used herein, the terms "treat," "treatment," "treating," or "amelioration" when used in reference to a disease, disorder or medical condition, refer to both therapeutic treatment and prophylactic or preventative measures, wherein the object is to reverse, alleviate, ameliorate, inhibit, lessen, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a disease, disorder or medical condition is reduced or halted. That is, "treatment" includes not just the improvement of symptoms or markers, but also a cessation or at least slowing of progress or worsening of symptoms that would be expected in the absence of treatment. Also, "treatment" may mean to pursue or obtain beneficial results, or lower the chances of the individual developing the condition even if the treatment is ultimately unsuccessful. Those in need of treatment include those already with the condition as well as those prone to have the condition or those in whom the condition is to be prevented. Non-limiting examples of therapeutic treatments include any one or more of coronary revascularization through stenting, coronary bypass grafting, or medical therapy, or combinations thereof. Non-limiting examples of medical therapies include statins, LDL lowering, beta blockers, ACE inhibitors, aspirin, etc. or combinations thereof.

"Beneficial results" or "desired results" may include, but are in no way limited to, lessening or alleviating the severity of the disease condition, preventing the disease condition from worsening, curing the disease condition, preventing the disease condition from developing, lowering the chances of a patient developing the disease condition, decreasing morbidity and mortality, and prolonging a patient's life or life expectancy. As non-limiting examples, "beneficial results" or "desired results" may be alleviation of one or more symptom(s), diminishment of extent of the deficit, stabilized (i.e., not worsening) state of a cardiovascular disease, delay or slowing of a cardiovascular disease, and amelioration or palliation of symptoms associated with a cardiovascular disease.

"Diseases", "conditions" and "disease conditions," as used herein may include, but are in no way limited to any form of cardiovascular conditions, diseases or disorders. Cardiovascular diseases are a class of diseases that involve the heart or blood vessels. Non-limiting examples of cardiovascular disease include: coronary artery disease, coronary heart disease, ischemic heart disease (IHD), cardiomyopathy, stroke, hypertensive heart disease, heart failure, pulmonary heart disease, ischemic syndrome, coronary microvascular disease, cardiac dysrhythmias, rheumatic heart disease (RHD), aortic aneurysms, cardiomyopathy, atrial fibrillation, congenital heart disease, endocarditis, inflammatory heart disease, endocarditis, inflammatory cardiomegaly, myocarditis, valvular heart disease, cerebrovascular disease, and peripheral artery disease (PAD).

As used herein, the term "administering," refers to the placement an agent as disclosed herein into a subject by a method or route which results in at least partial localization of the agents at a desired site. "Route of administration" may refer to any administration pathway known in the art, including but not limited to aerosol, nasal, via inhalation, oral, anal, intra-anal, peri-anal, transmucosal, transdermal, parenteral, enteral, topical or local. "Parenteral" refers to a route of administration that is generally associated with injection, including intratumoral, intracranial, intraventricular, intrathecal, epidural, intradural, intraorbital, infusion, intracapsular, intracardiac, intradermal, intramuscular, intraperitoneal, intrapulmonary, intraspinal, intrasternal, intrathecal, intrauterine, intravascular, intravenous, intraarterial, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the topical route, the pharmaceutical compositions can be in the form of aerosol, lotion, cream, gel, ointment, suspensions, solutions or emulsions. In accordance with the present invention, "administering" can be self-administering. For example, it is considered as "administering" that a subject consumes a composition as disclosed herein.

The term "sample" or "biological sample" as used herein denotes a sample taken or isolated from a biological organism. Exemplary biological samples include, but are not limited to, cheek swab; mucus; whole blood, blood, serum; plasma; urine; saliva; semen; lymph; fecal extract; sputum; other body fluid or biofluid; cell sample; and tissue sample etc. The term also includes a mixture of the above-mentioned samples. The term "sample" also includes untreated or pretreated (or pre-processed) biological samples. In some embodiments, a sample can comprise one or more cells from the subject.

As used herein, a "subject" means a human or animal. Usually the animal is a vertebrate such as a primate, rodent, domestic animal or game animal. Primates include chimpanzees, cynomolgus monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples. In addition, the methods described herein can be used to treat domesticated animals and/or pets.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

A subject can be one who has been previously diagnosed with or identified as suffering from or having a condition in need of treatment (e.g., a cardiovascular disease) or one or more complications related to the condition, and optionally, have already undergone treatment for the condition or the one or more complications related to the condition. Alternatively, a subject can also be one who has not been previously diagnosed as having a condition or one or more complications related to the condition. For example, a subject can be one who exhibits one or more risk factors for a condition or one or more complications related to the condition or a subject who does not exhibit risk factors. A "subject in need" of treatment for a particular condition can be a subject suspected of having that condition, diagnosed as having that condition, already treated or being treated for that condition, not treated for that condition, or at risk of developing that condition.

The term "statistically significant" or "significantly" refers to statistical evidence that there is a difference. It is defined as the probability of making a decision to reject the null hypothesis when the null hypothesis is actually true. The decision is often made using the p-value.

The term "functional" when used in conjunction with "equivalent", "analog", "derivative" or "variant" or "fragment" refers to an entity or molecule which possess a biological activity that is substantially similar to a biological activity of the entity or molecule of which it is an equivalent, analog, derivative, variant or fragment thereof.

As used herein, "remote territory" means normal myocardial territory that is not affected by cardiovascular disease.

As used herein, "affected territory" means abnormal myocardial territory that is affected by cardiovascular disease.

As used herein, "motion-corrected" means that the raw MM data that is acquired in the presence of cardiac and respiratory motion is retrospectively processed post imaging to remove the motion information which would otherwise appear as image artifacts and confound the interpretation.

As used herein, "registration" or "registered" or "registering" means that multiple images are acquired and the image with least motion (reference image) is first identified and then the remaining acquisitions are related back to the reference image to alter the image features with motion so as to map the images with motion to derive motion-corrected images. The process of mapping back to the reference images is referred to as registration herein.

As used herein, "rest" means before administration of a vasodilator.

As used herein, "rest image" means an image obtained before administration of a vasodilator.

As used herein, "stress" means after administration of a vasodilator.

As used herein, "stress image" means an image obtained after administration of a vasodilator.

As used herein, "ms" means milliseconds. For example, see FIG. 1.

Figure 3A:
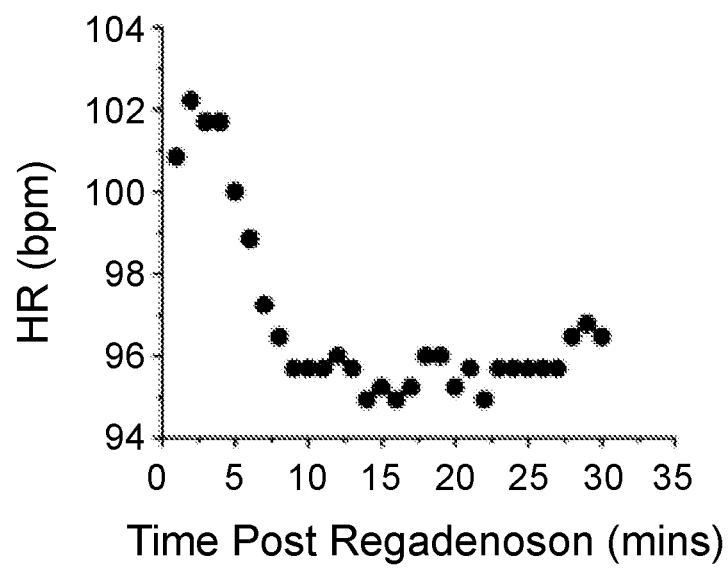
FIG. 3A-FIG. 3B illustrate, in accordance with various embodiments of the invention, heart-rate response and the BOLD image quality influence by different imaging time points. Significant heart-rate (HR) variation is observed in an animal for the first 5 minutes after regadenoson administration in FIG. 3A. The affected BOLD image quality due to imperfect imaging condition is shown in FIG. 3B.
Figure 3B:
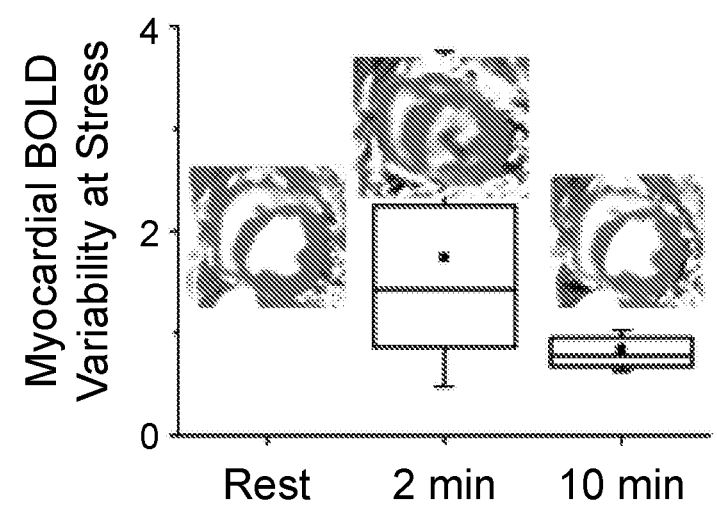

As used herein, "min" or "mins" means minute or minutes. For example, see FIG. 3A and FIG. 3B.

As used herein, "bpm" means beats per minute. For example, see FIG. 3A.

As used herein, "(ml/min/g)" means (milliliter/minute/gram). For example, see FIG. 2A.

As used herein, "(ml/mg/min)" means (milliliter/milligram/minute). For example, see FIG. 11.

Vascular reactivity may be monitored by characterization of myocardial perfusion reserve, which is defined as a ratio of myocardial perfusion at stress to myocardial perfusion at rest. In healthy subjects the ratio may vary from 2:1 to 6:1. The ratio diminishes with disease. A decrease in this ratio to 2:1 or below from the healthy level is considered clinically significant and indicative of poor vascular reactivity. Also, vascular reactivity may be monitored via differential absolute perfusion, which may be obtained using imaging methods such as first pass perfusion, SPECT/PET, CT perfusion or echocardiography in units of ml/sec/g (milliliter/second/gram) of tissue.

A coronary vasoreactive response (or cardiac stress response or hyperemic response) means a type and/or quantum of vasoreactive response elicited by cardiac stress testing (e.g. exercise or administration of a hyperemic drug) as demonstrable in an imaging study using one or more diagnostic imaging parameters of the type suitable to diagnose coronary vascular disease. For example, with respect to PET and SPECT, a normal response would be considered a four to five fold increase in blood flow. With respect to BOLD MM imaging, a 10-12% increase in BOLD signal would be considered normal.

Disease-associated responses are those which are not normal in varying significant degrees. As evidence of disease, benchmarks may be adopted to categorize differences which represent a clear-cut diagnosis or a progression of disease that warrants greater follow-up or more proactive treatment. A benchmark, may be for example, a less than two-fold increase in blood flow as measured by PET or SPECT (typically measured in ml. of blood/min/gm of tissue). Accordingly, a benchmark represents a change from a value that clinicians describe as "normal". For example, a change from "normal" which is at least statistically significant, and optionally is also comparable to a standard for cardiac stress testing adopted by clinicians with respect to inducing stress, represents a clear-cut benchmark for using exercise or a hyperemic drug as a vasoactive stress stimulus.

The current BOLD MRI imaging protocols typically utilize adenosine or regadenoson to achieve peak vasodilation prior to starting the MRI acquisition. However, during the acquisition period, unpredictable changes in heart rate and complex cardiac motion lead to unavoidable image artifacts. The inventors have developed a new approach for reliably imaging changes in myocardial blood flow and oxygenation in the setting of ischemic heart disease by taking advantage of the long lasting effects of regadenoson to retain hyperemic blood flow in the heart. This new approach enables cardiac blood-oxygen level dependent (BOLD) MRI to accurately detect ischemic heart disease without contrast agents.

The inventor's approach improves the image quality of BOLD images specifically during stress. The inventors achieve this by demonstrating that the myocardial blood flow following regadenoson infusion is retained above 2-fold relative to rest (a key conditions for stress imaging) even 10-15 minutes post regadenoson infusion. Notably during this period, even if the heart rates are high, MRI acquisition could be tuned adequately to capture myocardial hyperemia with markedly reduced image artifacts. This also improves patient comfort since cardiac stress is induced outside the MRI chamber.

In various embodiments, the present invention provides a method of imaging a subject's cardiovascular system. The method may consist of or may consist essentially of or may comprise: (a) imaging the subject's cardiovascular system at rest; (b) administering a vasodilator to the subject; and (c) imaging the subject's cardiovascular system after administering the vasodilator. In various embodiments, step (c) is performed about 5-6, 6-7, 7-8, 8-9, 9-10, 10-11, 11-12, 13-14, 14-15, 15-16, 16-17, 18-19, 19-20, 20-21, 21-22, 22-23, 23-24, or 24-25 minutes after step (b). In various embodiments, step (c) is performed about 10, 11, 12, 13, 14, or 15 minutes after step (b). In various embodiments, the method further comprises assessing vascular activity based on the imaging results at rest and after administering the vasodilator. For non-limiting examples, hyperemia response and/or myocardial perfusion reserve can be calculated from the imaging results at rest and after administering the vasodilator. In various embodiments, abnormal vascular activity indicates the presence of a cardiovascular disease or likelihood to develop a cardiovascular disease. In some embodiments, decreased vascular activity indicates the presence of a cardiovascular disease or likelihood to develop a cardiovascular disease. In other embodiments, increased vascular activity indicates the presence of a cardiovascular disease or likelihood to develop a cardiovascular disease.

In various embodiments, the present invention provides a blood oxygen level dependent (BOLD) magnetic resonance imaging (MM) method for obtaining one or more coronary dynamic parameters of a subject's cardiovascular system, comprising: (a) imaging the subject's cardiovascular system at rest to obtain a rest image; (b) administering an effective amount of a vasodilator to the subject, wherein the vasodilator has an extended vasodilatory state; (c) obtaining a series of images of the subject's cardiovascular system to obtain a plurality of stress images; (d) registering the stress images to the rest image to obtain a plurality of motion-corrected images; (e) applying the motion-corrected images to a first mathematical model; and (f) extracting the one or more coronary dynamic parameters from the first mathematical model.

In some embodiments, the method further comprises diagnosing the subject as having a cardiovascular disease. In some embodiments, the method further comprises prognosing the subject as being likely to develop a cardiovascular disease. In some embodiments, the method further comprises prognosing the subject as having a higher probability of developing a cardiovascular disease as compared to a healthy subject. In various embodiments, the diagnosis and/or prognosis is based on the imaging results at rest and after administering the vasodilator. In some embodiments, the method further comprises administering a treatment of the cardiovascular disease to the subject, thereby treating the cardiovascular disease.

In various embodiments, the cardiovascular disease is coronary artery disease, coronary heart disease, ischemic heart disease (IHD), cardiomyopathy, stroke, hypertensive heart disease, heart failure, pulmonary heart disease, ischemic syndrome, coronary microvascular disease, cardiac dysrhythmias, rheumatic heart disease (RHD), aortic aneurysms, cardiomyopathy, atrial fibrillation, congenital heart disease, endocarditis, inflammatory heart disease, endocarditis, inflammatory cardiomegaly, myocarditis, valvular heart disease, cerebrovascular disease, peripheral artery disease (PAD), infarcted myocardium, or a combination thereof.

In various embodiments, the cardiovascular disease is infarcted myocardium. In various embodiments, the cardiovascular disease is ischemic heart disease (IHD). In various embodiments, the cardiovascular disease is myocardium affected by ischemic heart disease. In various embodiments, the cardiovascular disease is ischemic myocardium. In various embodiments, the cardiovascular disease is ischemic myocardium affected by coronary narrowing and microvascular disease.

In various embodiments, the subject is a human. In various embodiments, the subject is a mammalian subject including but not limited to human, monkey, ape, dog, cat, cow, horse, goat, pig, rabbit, mouse and rat.

In various embodiments, the vasodilator induces hyperemia. In various embodiments, hyperemia response is reduced or compromised in subjects with cardiovascular diseases as compared to healthy subjects. As a non-limiting example, coronary artery disease leads to narrowing of the small blood vessels that supply blood and oxygen to the heart, and hence is expected to reduce hyperemic response and the perfusion reserve.

In various embodiments, the vasodilator is a selective A2A adenosine receptor agonist. In some embodiments, the selective A2A adenosine receptor agonist is regadenoson, or a functional equivalent, analog, derivative or salt of regadenoson. In other embodiments, the selective A2A adenosine receptor agonist is binodenoson, or a functional equivalent, analog, derivative or salt of binodenoson. In still other embodiments, the selective A2A adenosine receptor agonist is apadenoson, or a functional equivalent, analog, derivative or salt of apadenoson.

In various embodiments, the vasodilator is selected from regadenoson, binodenoson, apadenoson, and dipyridamole. In various embodiments the vasodilator is regadenoson. In various embodiments the vasodilator is binodenoson. In various embodiments the vasodilator is apadenoson. In various embodiments the vasodilator is dipyridamole.

Typical dosages of an effective amount of the vasodilator can be in their ranges recommended by the manufacturer where known vasodilators are used, and also as indicated to the skilled artisan by the responses in animal models or human subjects. Such dosages typically can be reduced by up to about an order of magnitude in concentration or amount without losing relevant biological activity. The actual dosage can depend upon the judgment of the physician, the condition of the patient, and the effectiveness of the imaging method based, for example, on the effectiveness observed in relevant and appropriate animal models. In various embodiments, the vasodilator may be administered once a day (SID/QD), twice a day (BID), three times a day (TID), four times a day (QID), or more, so as to administer an effective amount of the vasodilator to the subject, where the effective amount is any one or more of the doses described herein. In various embodiments, the vasodilator may be administered once, twice, three or more times.

In various embodiments, the vasodilator is administered at about 0.01-0.02, 0.02-0.03, 0.03-0.04, 0.04-0.05, 0.05-0.06, 0.06-0.07, 0.07-0.08, 0.08-0.09, 0.09-0.1, 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 5-6, 6-7, 7-8, 8-9, or 9-10 mg, or a combination thereof. In various embodiments, the vasodilator is administered at about 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 5-6, 6-7, 7-8, 8-9, 9-10, 10-20, 20-30, 30-40, 40-50, 50-60, 60-70, 70-80, 80-90, or 90-100 µg/kg body weight, or a combination thereof.

In accordance with the invention, the vasodilator may be administered using the appropriate modes of administration, for instance, the modes of administration recommended by the manufacturer for each of the vasodilator. In accordance with the invention, various routes may be utilized to administer the vasodilator of the claimed methods, including but not limited to intratumoral, intravascular, intravenous, intraarterial, intramuscular, subcutaneous, intraperitoneal, aerosol, nasal, via inhalation, oral, transmucosal, transdermal, parenteral, implantable pump or reservoir, continuous infusion, enteral application, topical application, local application, capsules and/or injections. In various embodiments, the vasodilator is administered intravascularly, intravenously, or intraarterially. In various embodiments, the vasodilator is administered intravascularly, intravenously, intraarterially, or intracoronary.

In various embodiments, the vasodilator is administered as a single bolus. In various embodiments, the single bolus is injected intravascularly, intravenously, or intraarterially to the subject. In various embodiments, the single bolus is injected intravascularly, intravenously, intraarterially, or intracoronary. In some embodiments, the single bolus is injected intravenously to the subject. In various embodiments, the single bolus comprises about 0.01-0.02, 0.02-0.03, 0.03-0.04, 0.04-0.05, 0.05-0.06, 0.06-0.07, 0.07-0.08, 0.08-0.09, 0.09-0.1, 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 5-6, 6-7, 7-8, 8-9, or 9-10 mg of the vasodilator.

In various embodiments, the vasodilator is administered as a continuous infusion. In various embodiments, the vasodilator can be administered as a continuous infusion using a programmable continuous infusion ambulatory pump or iv infusion bags or any other means known in the art. In various embodiments, the exact dosage range of the vasodilator administered as a continuous infusion will depend on the age, body weight, and/or condition of the subject being treated. As a non-limiting example, continuous infusion of adenosine is typically <240 mg/kg/min (this is two times the current dose). As a non-limiting example, continuous infusion with regadenoson should be <0.4 mg (accumulated dose over 30 minutes).

In various embodiments, no radioactive tracer or contrast agent is administered to the subject. In various embodiments, imaging the subject's cardiovascular system comprises imaging the subject's heart. In various embodiments, imaging the subject's cardiovascular system comprises imaging the subject's coronary arteries. In various embodiments, imaging the subject's cardiovascular system comprises imaging the subject's myocardium. In various embodiments, imaging the subject's myocardium comprises (i) obtaining free-breathing cardiac phase resolved 2D or 3D myocardial BOLD images; (ii) registering and segmenting the BOLD images to obtain the myocardial dynamic volume; and (iii) identifying ischemic territory and quantify image volume.

In various embodiments, imaging the subject's cardiovascular system comprises one or more imaging modalities. Examples of suitable imaging modalities include but are not limited to using positron emission tomography (PET), single photon emission computed tomography (SPECT), computed tomography (CT), magnetic resonance imaging (MM), first-pass perfusion magnetic resonance imaging (FPP-MRI), functional magnetic resonance imaging (fMRI), blood-oxygen-level dependent (BOLD) imaging, electron-beam computed tomography (EBCT), electron spin resonance (ESR), positron emission tomography/computed tomography (PET/CT), single photon emission computed tomography/computed tomography (SPECT/CT), positron emission tomography/magnetic resonance (PET/MR), and single photon emission computed tomography/magnetic resonance (SPECT/MR), and their various combinations. In one embodiment, BOLD imaging is used for imaging the subject's cardiovascular system.

In various embodiments, imaging the subject's cardiovascular system comprises blood-oxygen-level dependent (BOLD) magnetic resonance imaging (MRI) of the subject's cardiovascular system. In various embodiments, imaging the subject's cardiovascular system comprises performing myocardial perfusion imaging (MPI). In various embodiments, MPI is performed using blood-oxygen-level dependent (BOLD) magnetic resonance imaging (MM). In some embodiments, the method further comprises calculating myocardial BOLD response.

In some embodiments, a method described herein may be performed at the prevention stage of a condition (i.e., when the subject has not developed the condition but is likely to or in the process of developing the condition). In other embodiments, a method described herein may be performed at the treatment stage of a condition (i.e., when the subject has already developed the condition).

In some embodiments, the BOLD MRI used for imaging the subject's cardiovascular system is non-contrast $T_2$, $T_2^*$, or $T_1$ mapping (for example at 1.5T or 3T), which does not require exogenous contrast media. Therefore, the technique can be safely used even in patients for whom Late Gadolinium Enhancement (LGE) imaging and contrast-enhanced $T_1$ mapping are contraindicated. In various embodiments, the BOLD MRI used for imaging the subject's cardiovascular system is any one or more of non-contrast $T_1$-mapping, $T_1$-weighted imaging, inversion-recovery prepared $T_1$-weighted imaging, $T_2$-weighted images, $T_2$ maps, $T_2^*$-weighted images, $T_2^*$ maps, diffusion-weighted images, apparent-diffusion-coefficient (ADC) maps, steady-state free precession CINE images, steady-state free precession non-CINE images, steady-state free precession coherent images, incoherent steady-state free precession images, myocardial tags, magnetization transfer (MT) weighted and MT rate (MTR) images, or a combination thereof, which does not require exogenous contrast media.

In various embodiments, a method described herein may be performed once, twice, three or more times. In various embodiments, a method described herein may be performed 1-3 times per day, 1-7 times per week, 1-9 times per month, or 1-12 times per year. In various embodiments, a method described herein may be performed for about 1-6 hours, 7-12 hours, 13-18 hours, 19-24 hours, 1-10 days, 10-20 days, 20-30 days, 30-40 days, 40-50 days, 50-60 days, 60-70 days, 70-80 days, 80-90 days, 90-100 days, 1-6 months, 6-12 months, or 1-5 years.

In some embodiments, a non-contrast approach is used for imaging the subject's cardiovascular system, wherein the non-contrast approach includes but is not limited to blood oxygen level dependent (BOLD) magnetic resonance imaging (MM) or Arterial Spin Labeling (ASL) magnetic resonance imaging (MRI). In some embodiments, a non-contrast approach is used for imaging the subject's cardiovascular system, wherein the non-contrast approach is blood oxygen level dependent (BOLD) magnetic resonance imaging (MRI). In some embodiments, a non-contrast approach is used for imaging the subject's cardiovascular system, wherein the non-contrast approach is Arterial Spin Labeling (ASL) magnetic resonance imaging (MRI), In Arterial Spin Labeling (ASL) magnetic resonance imaging (MRI), Q is a time dependent measurement of myocardial blood flow (MBF) and $Q_o$ is the baseline MBF.

Arterial spin labeling is a cardiovascular magnetic resonance (CMR) technique for quantifying tissue blood flow, non-invasively and without contrast agents (Kober F, Jao T, Troalen T, Nayak K S, Myocardial arterial spin labeling. Journal of Cardiovascular Magnetic Resonance 2016; 18:22, 1-16. Radiofrequency pulses are used to modify the longitudinal magnetization of arterial blood, creating an endogenous label (or tracer) that decays with the time-constant equal to the T1 relaxation time, about 1.5 seconds for blood at 3 Tesla. After a delay to allow labeled blood to flow into the target tissue, images are acquired that reflect inflow of labeled blood as well as static tissue whose magnetization exchanges with that of the inflowing blood. A second set of images is acquired in the absence of a preceding labeling pulse. The difference between these two image sets reflects the amount of labeled blood that has been delivered to the imaging region, and with appropriate labeling, imaging, and perfusion model, can be made directly proportional to tissue blood flow. In some embodiments, a non-contrast approach used for imaging the subject's cardiovascular system is native T1-weighted or T1 mapping to assess blood flow changes.

In various embodiments, the time interval between each image obtained during imaging is 0.001 second-30 minutes, 0.001 second-20 minutes, 0.001 second-15 minutes, 0.001 second-10 minutes, 0.001 second-5 minutes, 0.001 second-1 minute, 0.01 second-30 minutes, 0.01 second-20 minutes, 0.01 second-15 minutes, 0.01 second-10 minutes, 0.01 second-5 minutes, 0.01 second-1 minute, 0.1 second-30 minutes, 0.1 second-20 minutes, 0.1 second-15 minutes, 0.1 second-10 minutes, 0.1 second-5 minutes, 0.1 second-1 minute, 1 second-30 minutes, 1 second-20 minutes, 1 second-15 minutes, 1 second-10 minutes, 1 second-5 minutes, or 1 second-1 minute, or a combination thereof. In various embodiments, the time interval between each image obtained during imaging is 1 minute-30 minutes, 1 minute-20 minutes, 1 minute-15 minutes, 1 minute-10 minutes, 1 minute-9 minutes, 1 minute-8 minutes, 1 minute-7 minutes, 1 minute-6 minutes, 1 minute-5 minutes, 1 minute-4 minutes, 1 minute-3 minutes, 1 minute-2 minutes, 2 minutes-30 minutes, 2 minutes-20 minutes, 2 minutes-15 minutes, 2 minutes-10 minutes, 2 minutes-9 minutes, 2 minutes-8 minutes, 2 minutes-7 minutes, 2 minutes-6 minutes, 2 minutes-5 minutes, 2 minutes-4 minutes, 2 minutes-3 minutes, 3 minutes-30 minutes, 3 minutes-20 minutes, 3 minutes-15 minutes, 3 minutes-10 minutes, 3 minutes-9 minutes, 3 minutes-8 minutes, 3 minutes-7 minutes, 3 minutes-6 minutes, 3 minutes-5 minutes, 3 minutes-4 minutes, 4 minutes-30 minutes, 4 minutes-20 minutes, 4 minutes-15 minutes, 4 minutes-10 minutes, 4 minutes-9 minutes, 4 minutes-8 minutes, 4 minutes-7 minutes, 4 minutes-6 minutes, 4 minutes-5 minutes, 5 minutes-30 minutes, 5 minutes-20 minutes, 5 minutes-15 minutes, 5 minutes-10 minutes, 5 minutes-9 minutes, 5 minutes-8 minutes, 5 minutes-7 minutes, 5 minutes-6 minutes, 6 minutes-30 minutes, 6 minutes-20 minutes, 6 minutes-15 minutes, 6 minutes-10 minutes, 6 minutes-9 minutes, 6 minutes-8 minutes, 6 minutes-7 minutes, 7 minutes-30 minutes, 7 minutes-20 minutes, 7 minutes-15 minutes, 7 minutes-10 minutes, 7 minutes-9 minutes, 7 minutes-8 minutes, 8 minutes-30 minutes, 8 minutes-20 minutes, 8 minutes-15 minutes, 8 minutes-10 minutes, 8 minutes-9 minutes, 9 minutes-30 minutes, 9 minutes-20 minutes, 9 minutes-15 minutes, or 9 minutes-10 minutes, or a combination thereof.

In various embodiments, one or more motion corrected images are applied to a first mathematical model. An example of a suitable first mathematical model includes but is not limited to a mono-exponential model $T_2(t)=T_{2o}+\Delta T_{2max}\exp(-t/\tau)$, wherein $T_2$ is a transverse relaxation time, t is a time period following administration of a vasodilator to the subject, $T_{2o}$ is an estimate of baseline $T_2$, $\Delta T_{2max}$ is an estimate of maximum $T_2$ change from rest, and $\tau$ is an estimate of coronary relaxation time constant. In various embodiments, other mathematical models besides the mono-exponential model $T_2(t)=T_{2o}+\Delta T_{2max}\exp(-t/\tau)$ may also be used as the first mathematical model.

In various embodiments, one or more coronary dynamic parameters are extracted from the first mathematical model. Examples of suitable coronary dynamic parameters include but are not limited to $T_2$, t, $T_{2o}$, $\Delta T_{2max}$, $\tau$, $\Delta T_{2max}/T_{2o}$, $\Delta T_{2max}/\tau$, $(\tau \times \Delta T_{2max})$, $dT_2/dt$, or combinations thereof, wherein $T_2$ is a transverse relaxation time, t is a time period following administration of a vasodilator to the subject, $T_{2o}$ is an estimate of baseline $T_2$, $\Delta T_{2max}$ is an estimate of maximum $T_2$ change from rest, $\tau$ is an estimate of coronary relaxation time constant, $\Delta T_{2max}/T_{2o}$ represents relative change in BOLD contrast, $\Delta T_{2max}/\tau$ is dimensionless and represents the total dynamic range for myocardial BOLD response, and $dT_2/dt$ represents the rate of change in $T_2$ with respect to time.

In various embodiments, one or more of the coronary dynamic parameters or a combination thereof are applied to a second mathematical model. In various embodiments, the second mathematical model may be used to identify the territory of the myocardium with disease (affected territory) and/or the territory of the myocardium without disease (remote territory). In various embodiments, a second mathematical model may be used to obtain a reference value, wherein a change in one or more coronary dynamic parameters relative to the reference value is indicative of the cardiovascular disease in the subject's cardiovascular system.

In various embodiments, one or more of the coronary dynamic parameters or a combination thereof may be used in conjunction with empirical data or applied to empirical data and may be used to identify the territory of the myocardium with disease (affected territory) and/or the territory of the myocardium without disease (remote territory). In various embodiments, one or more of the coronary dynamic parameters or a combination thereof may be used in conjunction with empirical data or applied to empirical data to obtain a reference value, wherein a change in one or more coronary dynamic parameters relative to the reference value is indicative of the cardiovascular disease in the subject's cardiovascular system (Arnold J R, Karamitsos T D, Bhamra-Ariza P, Francis J M, Searle N, Robson M D, Howells R K, Choudhury R P, Rimoldi O E, Camici P G, Banning A P, Neubauer S, Jerosch-Herold M, Selvanayagam J B. Myocardial oxygenation in coronary artery disease: insights from blood oxygen level-dependent magnetic resonance imaging at 3 tesla. J. Am. Coll. Cardiol. 2012: 5:22:1954-1964; Parnham S, Gleadle J M, Bangalore S, Grover S, Perry R, Woodman R J, De Pasquale C G, Selvanayagam J P, Impaired Myocardial Oxygenation Response to Stress in Patients With Chronic Kidney Disease. J. Am. Heart. Assoc. 2015: 4(8):e002249; Karamitsos T D, Leccisotti L, Arnold J R, Recio-MNayoral A, Bhamra-Ariza P, Howells R K, Searle N, Robson M D, Rimoldi O E, Camici P G, Neubauer S, Selvanayagam J B, Relationship between regional myocardial oxygenation and perfusion in patients with coronary artery disease: insights from cardiovascular magnetic resonance and positron emission tomography. Cir. Cardiovasc. Imaging 2010: 3:1:32-40).

Examples of suitable second mathematical models include but are not limited to Gaussian mixture model (GMM), ARREAS model, support vector machines (SVM) model, or full width at half maximum (FWHM) model. Further non-limiting examples of suitable second mathematical models may be found in Methods Mol. Bio. 2012, 929, 583-600.

Gaussian mixture model (GMM) is a well-known segmentation model used to separate pixel-intensity values that conform to Gaussian distributions. In various embodiments, GMM can be applied to the coronary dynamic parameters or combinations of the coronary dynamic parameters. In one embodiment, the values for the coronary dynamic parameters $\Delta T_{2max}$ and $\Delta T_{2max}/T_{2o}$ obtained from each pixel in the myocardium were fitted to two Gaussian distributions, each Gaussian distribution having one mean. The GMM segmented the pixels into two clusters, one representing pixels corresponding to normal/healthy tissue and the other representing tissue affected by disease. The cluster of disease pixels was identified as the cluster with a lower mean value.

In various embodiments, the mean minus n standard deviation (mean-nSD) may be applied to the coronary dynamic parameters $\Delta T_{2max}$ and $\Delta T_{2max}/T_{2o}$ obtained from the Gaussian mixture model. The mean-nSD, where n is an integer (e.g., 1, 2, etc.) may be used to avoid cross talk between pixel-intensity clusters from the Gaussian mixture model to tighten up the cut-off between normal and disease pixels.

In various embodiments, without being bound by theory, Gaussian mixture model (GMM) was performed for each coronary dynamic parameter. Cut off values were identified between healthy and diseased myocardium. The GMM threshold identification included the following steps.

a. The dynamic parameters derived from the mono-exponential model were extracted from the myocardium with manual contouring of endo- and epi-myocardial contours.

b. A weighted sum of two component Gaussian densities as given by the equation:

$$p(x|\mu,\sigma)=\Sigma_i w_i g(x|\mu_i,\sigma_i)$$

were used to fit the extracted coronary dynamic parameters in the myocardium using minimum likelihood estimation, where p represents the summed density, x represents the fitted coronary dynamic parameters, i.e. $\Delta T_{2max}$ and $\Delta T_{2max}/T_{2o}$; i=1, 2; and g represents the component Gaussian densities. $g(x|\mu_i, \sigma_i)$ is defined as:

$$g(x|\mu_i, \sigma_i) = \frac{1}{|\sigma_i|^{1/2}}\exp\left\{-\frac{1}{2}(x-\mu_i)'\sigma_i^{-1}(x-\mu_i)\right\}$$

with mean value $\mu_i$ and covariance $\sigma_i$. w represents the mixture weights, wherein the mixture weights satisfy the constraint that $\Sigma_i w_i=1$.

c. From the fitted Gaussian densities, the one with a larger mean value was defined as the distribution of the normal myocardium and the corresponding pixels were identified as the normal territories.

d. Standard deviation was derived from the identified normal myocardial pixels using the mean-nSD model, wherein n=2.

e. Mean-2SD of the identified normal value was set as the cut off for each coronary dynamic parameter. The pixels with values smaller than mean-2SD were identified as the affected myocardium.

Gaussian mixture model (GMM) can be applied to multiple coronary dynamic parameters at the same time. In that case, μj will be a vector and a will be a matrix, which can be used to combine the coronary dynamic parameters to increase separability between normal and diseased values in a higher dimension.

Support Vector Machine (SVM) model is a state-of-the-art segmentation technique that has been successfully applied in classification and function estimation problems after their introduction by Vapnik within the context of statistical learning theory and structural risk minimization (Wang X Y, Wang, T, Bu J. Color image segmentation using pixel wise support vector machine classification. Pattern Recognition 2011; 44:4, 777-787). Vapnik constructed the standard SVM to separate training data into two classes. The goal of the SVM is to find the hyper-plane that maximizes the minimum distance between any data point. In feature space a SVM model takes the form $y(x)=\omega^T\phi(x)+b$, where y represents the corresponding target function, x represents the coronary dynamic parameters as described herein. The nonlinear mapping $\phi(-)$ maps the coronary dynamic parameters into a so-called higher dimensional feature space, b is the bias and co is a weight vector of the same dimension as the feature space. T represents transpose (which is an operator instead of a variable). In this space, a linear decision surface is constructed with special properties that ensure high generalization ability of the network. By use of a nonlinear kernel function, it is possible to compute a separating hyper-plane with a maximum margin in a feature space, where maximize the margin between normal and disease is defined as $2/\|\omega\|$.)

In various embodiments, a support vector machine (SVM) model is applied to input one or more coronary dynamic parameters (e.g., $\Delta T_{2max}$, $T_{2o}$, $\tau$) to separate healthy and diseased pixels using a predefined knowledge of how the system should behave (i.e., a training dataset). In the training phase, the SVM model identifies an optimal combination and a threshold of the one or more coronary dynamic parameters to best segment the healthy and diseased pixels. The combination may then be applied to new datasets to separate healthy and diseased pixels.

ARREAS model detects the affected territory in the rest and stress images (from end-systole or end-diastole) following the determination of a statistically derived threshold obtained from the rest images (Tsaftaris S A, Tang R, Zhou X, Li D, Dharmakumar R 2012; J. Magn. Reson. Imaging, 35: 1338-1348). Subsequently, by conditioning the affected (hypointense) territory to be contiguous, a case that is in line with expected physiology. The probability defined as follows:

$$(x; A, B, v) = \frac{\Gamma\left(\frac{v+1}{2}\right)}{B\sqrt{v\pi}\,\Gamma\left(\frac{v}{2}\right)}\left[\frac{v+\left(\frac{x-A}{B}\right)^2}{v}\right]^{-\left(\frac{v+1}{2}\right)},$$

where x is the input coronary dynamic parameters, A is the location, B is the scale, and $v>0$ is the shape parameter, respectively and $\Gamma(z)$ is the gamma function. If x follows a t-location-scaled distribution, with the parameters A, B, and v, then the transformed variable $(x-A)/B$ follows a Student's t-distribution with v degrees of freedom. The parameters A, B, and v of the distribution were determined on the basis of Maximum-Likelihood-Estimation. Using the location (A) and scale (B) parameters of the fitted distribution, the threshold T=A−B was computed and used to threshold both rest and stress images, identifying all pixels within the myocardium having values less than T (hypointense territories). In various embodiments, an ARREAS model is applied to input one or more coronary dynamic parameters (e.g., $\Delta T_{2max}$, $T_{2o}$, $\tau$, $\Delta T_{2max}/\tau$. In the ARREAS model, myocardial pixel intensities from rest images may be fitted to location-scaled t-distribution to estimate the location (A) and scale (B) parameters. A cut-off value of the input one or more coronary dynamic parameters for identifying disease may be defined from the model as described in the literature (Tsaftaris S A, Tang R, Zhou X, Li D, Dharmakumar R 2012; J. Magn. Reson. Imaging, 35: 1338-1348), using the location and scale parameters.

In various embodiments, an effective amount of a vasodilator is administered to the subject, wherein the vasodilator has an extended vasodilatory state. Examples of an extended vasodilatory state include but are not limited to a terminal half-life of 33-108 min for regadenoson (Al Jaroudi W, Iskandrian A E. Regadenoson: a new myocardial stress agent. Journal of the American College of Cardiology 2009; 54:1123-30), 10-120 min for binodenoson, 5 min for apadenoson, and 40 min to 10 hours for dipyridamole (Zoghbi G J, Iskandrian A E. Selective adenosine agonists and myocardial perfusion imaging. J. Nucl. Cardiol. 2012 19:1, 126-141).

In various embodiments, the vasodilator may be provided as pharmaceutical compositions. In various embodiments, the pharmaceutical compositions according to the invention may be formulated for delivery via any route of administration. "Route of administration" may refer to any administration pathway known in the art, including but not limited to aerosol, nasal, via inhalation, oral, transmucosal, transdermal, parenteral, enteral, topical or local. "Parenteral" refers to a route of administration that is generally associated with injection, including intracranial, intraventricular, intrathecal, epidural, intradural, intraorbital, infusion, intracapsular, intracardiac, intradermal, intramuscular, intraperitoneal, intrapulmonary, intraspinal, intrasternal, intrathecal, intrauterine, intravascular, intravenous, intraarterial, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the topical route, the pharmaceutical compositions can be in the form of aerosol, lotion, cream, gel, ointment, suspensions, solutions or emulsions. Methods for these administrations are known to one skilled in the art. In certain embodiments, the pharmaceutical compositions are formulated for intravascular, intravenous, or intraarterial administration. In one embodiment, the pharmaceutical compositions are formulated for intravenous administration as a single bolus.

In various embodiments, the pharmaceutical compositions according to the invention can contain any pharmaceutically acceptable excipient. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous. Examples of excipients include but are not limited to starches, sugars, microcrystalline cellulose, diluents, granulating agents, lubricants, binders, disintegrating agents, wetting agents, emulsifiers, coloring agents, release agents, coating agents, sweetening agents, flavoring agents, perfuming agents, preservatives, antioxidants, plasticizers, gelling agents, thickeners, hardeners, setting agents, suspending agents, surfactants, humectants, carriers, stabilizers, and combinations thereof.

In various embodiments, the pharmaceutical compositions according to the invention can contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its imaging benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical compositions are made following the conventional techniques of pharmacy involving dry milling, mixing, and blending for powder forms; milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a stress-imaging effective amount. The precise stress-imaging effective amount is that amount of the composition that will yield the most effective results in terms of imaging the subject's cardiovascular system under stress. This amount will vary depending upon a variety of factors, including but not limited to the characteristics of the vasodilator (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a stress-imaging effective amount through routine experimentation, for instance, by monitoring image quality and adjusting the dosage accordingly.

Before administration to patients, formulants may be added to the composition. A liquid formulation may be preferred. For example, these formulants may include oils, polymers, vitamins, carbohydrates, amino acids, salts, buffers, albumin, surfactants, bulking agents or combinations thereof.

Carbohydrate formulants include sugar or sugar alcohols such as monosaccharides, disaccharides, or polysaccharides, or water soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxethyl starch and carboxymethylcellulose, or mixtures thereof. "Sugar alcohol" is defined as a C4 to C8 hydrocarbon having an —OH group and includes galactitol, inositol, mannitol, xylitol, sorbitol, glycerol, and arabitol. These sugars or sugar alcohols mentioned above may be used individually or in combination. There is no fixed limit to amount used as long as the sugar or sugar alcohol is soluble in the aqueous preparation. In one embodiment, the sugar or sugar alcohol concentration is between 1.0 w/v % and 7.0 w/v %, more preferable between 2.0 and 6.0 w/v %.

Amino acids formulants include levorotary (L) forms of carnitine, arginine, and betaine; however, other amino acids may be added.

Polymers formulants include polyvinylpyrrolidone (PVP) with an average molecular weight between 2,000 and 3,000, or polyethylene glycol (PEG) with an average molecular weight between 3,000 and 5,000.

It is also preferred to use a buffer in the composition to minimize pH changes in the solution before lyophilization or after reconstitution. Most any physiological buffer may be used including but not limited to citrate, phosphate, succinate, and glutamate buffers or mixtures thereof. In some embodiments, the concentration is from 0.01 to 0.3 molar. Surfactants that can be added to the formulation are shown in EP Nos. 270,799 and 268, 110.

Another drug delivery system for increasing circulatory half-life is the liposome. Methods of preparing liposome delivery systems are discussed in Gabizon et al., Cancer Research (1982) 42:4734; Cafiso, Biochem Biophys Acta (1981) 649:129; and Szoka, Ann Rev Biophys Eng (1980) 9:467. Other drug delivery systems are known in the art and are described in, e.g., Poznansky et al., DRUG DELIVERY SYSTEMS (R. L. Juliano, ed., Oxford, N.Y. 1980), pp. 253-315; M. L. Poznansky, Pharm Revs (1984) 36:277.

After the liquid pharmaceutical composition is prepared, it may be lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is administered to subjects using those methods that are known to those skilled in the art.

The compositions of the invention may be sterilized by conventional, well-known sterilization techniques. The resulting solutions may be packaged for use or filtered under aseptic conditions and lyophilized, the lyophilized preparation being combined with a sterile solution prior to administration. The compositions may contain pharmaceutically-acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, and stabilizers (e.g., 1-20% maltose, etc.).

Many variations and alternative elements have been disclosed in embodiments of the present invention. Still further variations and alternate elements will be apparent to one of skill in the art. Among these variations, without limitation, is the selection of steps, pharmaceutical compositions, administration routes and devices, imaging technologies for the inventive methods, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

EXAMPLES

The invention will be further explained by the following Examples, which are intended to be purely exemplary of the invention, and should not be considered as limiting the invention in any way. The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

BOLD Cardiovascular Magnetic Resonance (BOLD CMR) is a non-contrast approach for examining myocardial perfusion but despite major technical advancements to date, its reliability remains weak. A key reason for this is the unpredictable cardiac motion during stress, which can lead to pronounced artifacts that confound/mask the true BOLD signal changes during hyperemia.

Recently, regadenoson has become the vasodilator of choice owing to greater patient tolerability and ease of use. The inventors demonstrated that at 10-mins post regadenoson administration (p.r.a), (a) BOLD CMR artifacts at stress are markedly reduced compared to those conventionally acquired at 2-mins p.r.a; and (b) that myocardial perfusion reserve (MPR) remains greater than 2.0 and is highly correlated with the BOLD effects estimated from T2 maps.

Canines (n=7) were studied in a PET/MR system. MR acquisitions were used to generate short-axis 2D $T_2$ maps; and the PET acquisitions following $^{13}$N-ammonia infusion were used to quantify myocardial blood flow (MBF). Initially, 2D $T_2$ maps and PET signals were acquired at rest. Subsequently, regadenoson (2.5 µg/kg) was administered. $T_2$ maps were acquired at 2- and 10-mins p.r.a and PET signals were acquired at 10-mins p.r.a. Standard deviation (σ) of myocardial $T_2$ values was measured at rest, 2- and 10-mins p.r.a from $T_2$ maps and were used to determine Myocardial BOLD Variability (MBV, defined as $\sigma T_2$(stress)/$\sigma T_2$(rest)) at 2- and 10-min p.r.a. Similarly, using the mean $T_2$ values, Myocardial BOLD Response (MBR, defined as $T_2$(stress)/$T_2$(rest)) was computed at 10-mins p.r.a. PET images were analyzed with qPET software to determine MBF and MPR at rest and 10-mins p.r.a and were regressed against MBR.

Figure 2A:
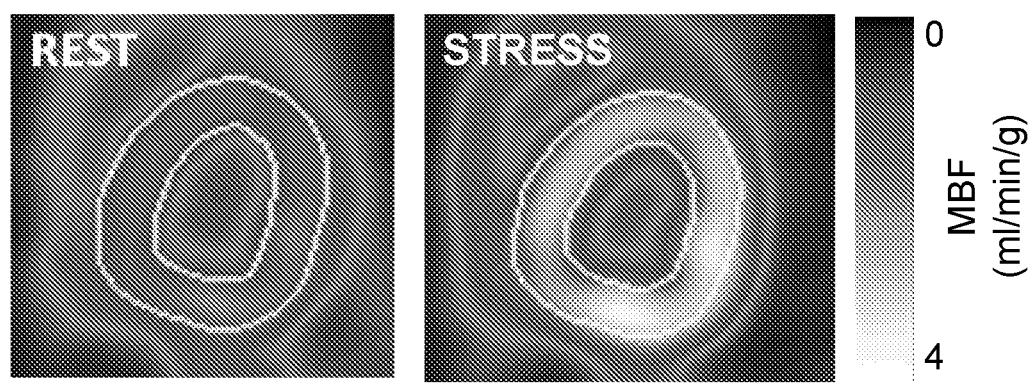
FIG. 2A-FIG. 2E illustrate, in accordance with various embodiments of the invention, N-ammonia PET myocardial blood flow and BOLD response at 10 mins post regadenoson administration (p.r.a.). Representative rest and stress (10 mins p.r.a) short-axis PET myocardial blood flow (MBF) and myocardial BOLD $T_2$ maps are shown in FIG. 2A and FIG. 2C. Both PET and BOLD images showed significant increase in MBF and BOLD response, respectively, at 10 mins p.r.a. compared to rest. Box plot of rest and stress MBF and myocardial $T_2$ across all animals are shown in FIG. 2B and FIG. 2D, respectively. Mean increase in MBF by a factor of 3.0 and a 9% $T_2$ elevation were observed on the PET and $T_2$ maps acquired at 10 min p.r.a. relative to rest. Results from regression analysis showed good correlation between PET myocardial perfusion reserve (MBF(stress)/MBF(rest)) and Myocardial BOLD Response (R=0.7, p<0.05.
Figure 2B:
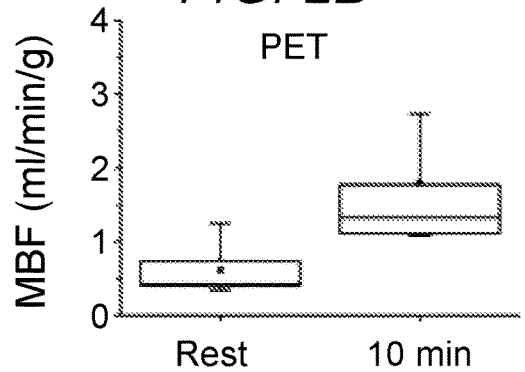
Figure 2C:
Figure 2D:
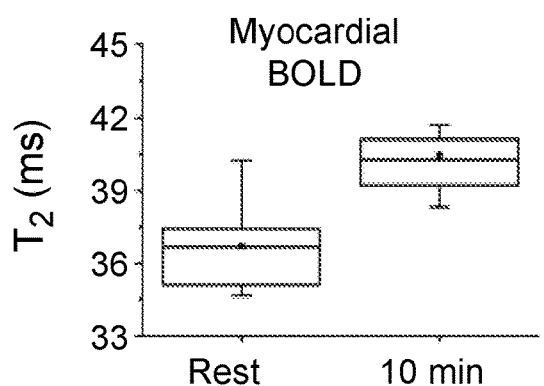
Figure 2E:
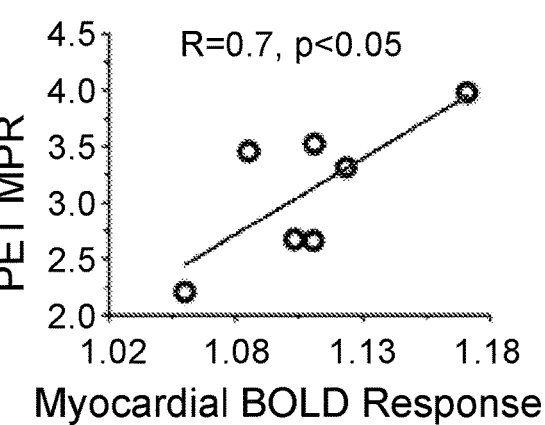

A box-plot of observed MBV at 2- and 10-mins p.r.a (and at rest, for reference), along with representative $T_2$ maps are shown in FIG. 1. Note the extensive artifacts present in the $T_2$ map at 2 min, which are absent in the $T_2$ maps acquired at rest and 10-mins p.r.a. MBV was significantly larger at 2-mins p.r.a (1.6±0.9) compared to 10-mins p.r.a (1.0±0.3) and rest (1.0); p<0.05 for both. Representative MBF at rest and 10-mins p.r.a. are shown in FIG. 2A. MBF at 10-min p.r.a (1.8±0.9 ml/min/g) was significantly higher than at rest (0.6±0.3 ml/min/g), p<0.05 (FIG. 2B). Mean MPR at 10-min p.r.a was 3.0. Corresponding BOLD images ($T_2$ maps) are shown in FIG. 2C. Myocardial $T_2$ at 10-min p.r.a (40.4±1.7 ms) was significantly higher than at rest (37.1±2.0 ms), p<0.05 (FIG. 2D). MBR was strongly correlated with MPR (R=0.7, p<0.05, FIG. 2E).

Myocardial BOLD images acquired at 10-min p.r.a (compared to 2-min p.r.a) can be free of image artifacts. MPR at 10-mins p.r.a can be consistently higher than 2.0 and is strongly correlated with MBR. These data support that delayed acquisition of BOLD CMR post regadenoson administration is a viable means for increasing the reliability of cardiac BOLD.

Example 2

Over the past two decades BOLD Cardiovascular Magnetic Resonance (BOLD CMR) has seen major progress in technical developments and advanced by a number of clinical validation studies. However, the reliability of BOLD CMR remains a key weakness for its widespread adoption for routine clinical use. Although technical developments as presented in our previous work have significantly improved imaging speed, coverage and helped to reduce imaging confounders, the unstable physiological conditions during vasodilator stress leads to significant variations in the BOLD measurements. Specifically, irregular cardiac motion, rapidly changing heart rate during acquisition and significantly shorter quiescent period contribute to motion artifacts, cardiac phase mismatch between rest and stress image, all of which lead to deterioration of BOLD images. This invariably masks the observed BOLD responses during stress and can diminish the reliability of the data interpretation.

Coronary Relaxation Dynamics in the Presence of Regadenoson. Regadenoson has become a popular stress agent (Zoghbi G J, Iskandrian A E. Selective adenosine agonists and myocardial perfusion imaging. J. Nucl. Cardiol. 2012 19:1, 126-141) owing to its specificity to $A_{2A}$ adenosine receptor (improving patient tolerability) and ease of administration (bolus injection rather than continuous infusion). However, a rapidly changing cardiac motion (FIG. 3A) post regadenoson administration can affect the conventional single time point BOLD imaging strategy in 2 ways: (i) irregular motion can lead to motion artifacts, can degrade image quality and result in cardiac phase mismatch (FIG. 3B) (Hsin-Jung Yang, Damini Dey, Jane M Sykes et al. Towards reliable myocardial blood-oxygen-level-dependent (BOLD) CMR using late effects of regadenoson with simultaneous 13n-amm. Journal of Cardiovascular Magnetic Resonance 2016; 18(Suppl 1):O19) and (ii) heart rate differences between rest to stress can confound the measured BOLD signal and mask the BOLD response.

Although advanced Magnetic Resonance (MR) technical development can overcome part of the challenges, the unpredictable cardiac motion can still undermine the robustness of the image quality and prolong the scan time. In this study, we hypothesized that continuous monitoring of the myocardial BOLD signal after regadenoson administration can improve the robustness of BOLD response extraction while preserving the sensitivity of peak vasodilation. To achieve this, we utilized a multiple measurement strategy to investigate the coronary dynamic after regadenoson administration and reduced the influence on the BOLD response from artifacts in a single image. We applied a mono-exponential decay model to extract the coronary dynamic parameters (CDPs), and derived the maximum BOLD response to compare with the conventional single time point method.

We studied healthy human volunteers, intact dogs and dogs with chronic myocardial infarction to evaluate the capability of BOLD CMR for characterizing the coronary dynamics. In the healthy subjects, global CDPs were extracted to show the feasibility of the method and the increased BOLD sensitivity. In the pathologic cases, CDPs were compared between remote and affected territories in segmental and pixel wise fashions to evaluate the capability of detecting abnormal myocardial territories.

Figure 4:
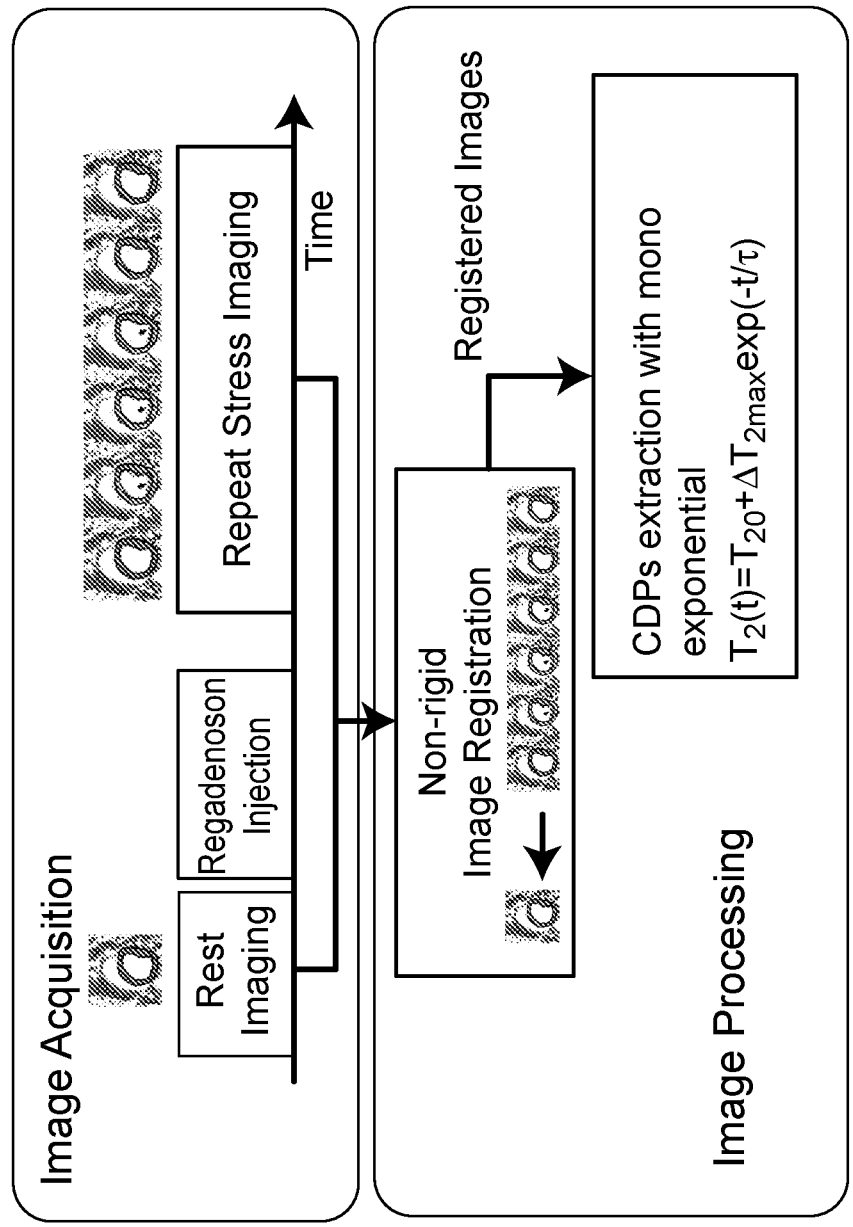
FIG. 4 illustrates, in accordance with various embodiments of the invention, an experimental flow chart. Rest BOLD images were acquired before regadenoson administration and repeat BOLD acquisitions starting from 2 minutes post the bolus regadenoson injection were performed. Images were acquired every 1-5 minutes for 30 minutes. The stress images were registered to the rest image using a non-rigid motion correction algorithm Avants B B, Tustison N J, Song G, Cook P A, Klein A, Gee J C. A reproducible evaluation of ANTs similarity metric performance in brain image registration. Neuroimage 2011; 54:2033-44). The motion corrected images were used to fit the coronary dynamics parameters with a mono-experimental model.

BOLD images were acquired at different time points before and after regadenoson administration to sample the rest and stress images, respectively. After bolus regadenoson injection, multiple stress images were acquired to sample the coronary dynamics curve for 30 minutes. All stress images were registered to the rest images with a non-rigid motion correction algorithm (Avants B B, Tustison N J, Song G, Cook P A, Klein A, Gee J C. A reproducible evaluation of ANTs similarity metric performance in brain image registration. Neuroimage 2011; 54:2033-44) to correct for motion-induced miss match between acquisitions. Motion corrected images were used to extract the CDPs throughout the stress period using a mono-exponential model (Felmlee M A, Morris M E, Mager D E. Mechanism-based pharmacodynamic modeling. Methods in molecular biology 2012; 929:583-600) ($T_2(t)=T_{2o}+\Delta T_{2max} \exp(-t/\tau)$). A flow chart of the experimental setup is depicted in FIG. 4.

In healthy volunteers and intact dogs, global CDPs were extracted from the myocardium. Maximum BOLD response was derived with CDPs ($MBR_{CDP}=\Delta T_{2max}/T_{2o} \times 100\%$) and compared with conventional myocardial BOLD response ($MBR_{con}$), which was derived as the $T_2$ elevation from rest to 2 minutes after regadenoson administration ($MBR_{conv}=[(StressT_2^{2min}/Rest\ T_2)-1] \times 100\%$). In the animals with coronary impairment, CDPs were measured in segmental and pixel-wise manner. Pixel-wised CDPs between remote and affected territories were segmented using SVMs to investigate the capability of separating diseased myocardium from the remote regions. In addition, CDPs were derived from subsets of BOLD images with different starting time points to probe the optimized setup of detecting affected territories. Details of each step are described in the following sections.

Experimental Subjects and animal preparation: We studied healthy human volunteers (n=6), intact dogs (n=7) and dogs with chronic infarctions (n=1). During imaging studies in animals, all animals were mechanically ventilated and anesthetized with propofol. In the dog with chronic infarction, the animal underwent an open chest ischemia reperfusion protocol (3 hours of ischemia followed by reperfusion), followed by 8-week recovery prior to imaging.

Figure 5:
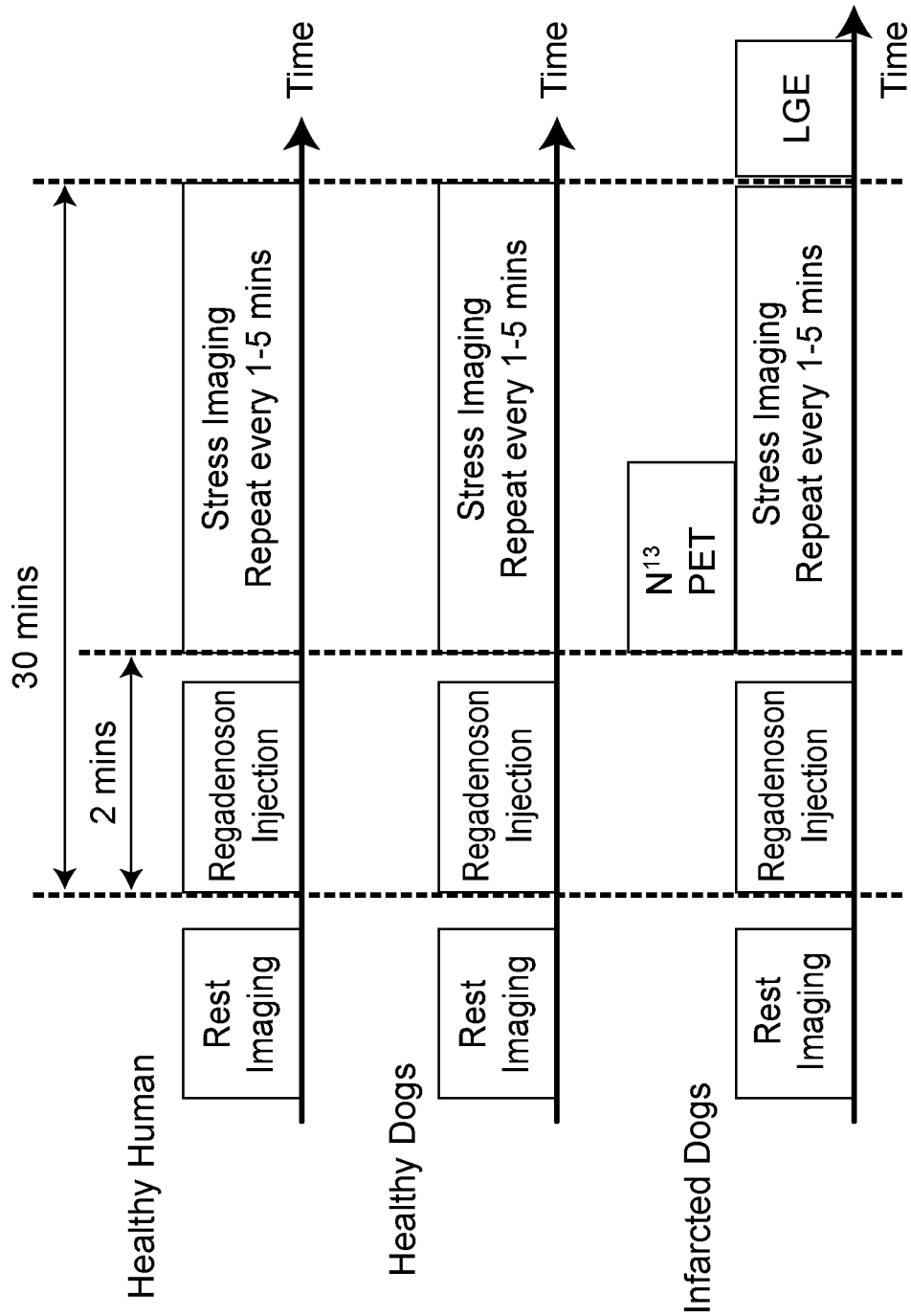
FIG. 5 illustrates, in accordance with various embodiments of the invention, the chronological order of image acquisition for each imaging group.

Image acquisition: Human studies were performed on a 3.0 T clinical MM system (MAGNETOM Verio®, Siemens Healthcare, Erlangen, Germany) and the animals were studied on a 3T whole body PET MR system (Biograph mMR, Siemens Healthcare, Erlangen, Germany). In all subjects, BOLD images were acquired with a commercially available 2D $T_2$ mapping sequence {Giri, 2009 #820}. In all studies, after localization and shimming, rest BOLD images were acquired under baseline followed by a bolus regadenoson injection. Post regadenoson administration, BOLD CMR images were acquired between 2 to 30 minutes after regadenoson injection with an interval of 1-5 minutes depending on the physiological and imaging condition. In the animal with chronic infarction, simultaneous $^{13}N$ ammonia PET images were acquired at 2 minutes post regadenoson administration to validate the hyperemic response from regadenoson. In addition, LGE images were acquired to identify the infarcted territories after all BOLD acquisitions were completed. Block representations of imaging protocols are illustrated in FIG. 5. Imaging parameters are listed as the following: T2 mapping: TR/TE=2.9 ms/1.1 ms, iPAT=2, partial Fourier=3/4, FA=35°, BW=1184 Hz/pixel, 86 lines per heartbeat (simulated rate 60/s), trigger pulse=4, FOV=288×360 mm², matrix size=154×192, and voxel size=2.5×1.7×6.0 mm³, $T_2$ preparation (as TEs)=0, 24, 55 ms.

Late Gadolinium Enhancement (LGE): PSIR LGE images were acquired 10 minutes after Gd-DTPA infusion (0.2 mmol/kg, gadoversetamide/Optimark, Mallinckrodt Inc., Hazelwood, Mo.), using non-selective inversion recovery preparation with GRE readout (TR/TE=3.2/1.5 ms, FA=20°, BW=586 Hz/pixel, matrix=96×192, in-plane resolution=1.3×1.3 mm²; and slice thickness=6.0 mm). A TI-scout sequence was used to find the optimal TI for nulling the healthy myocardium (240-270 ms).

Figure 6:
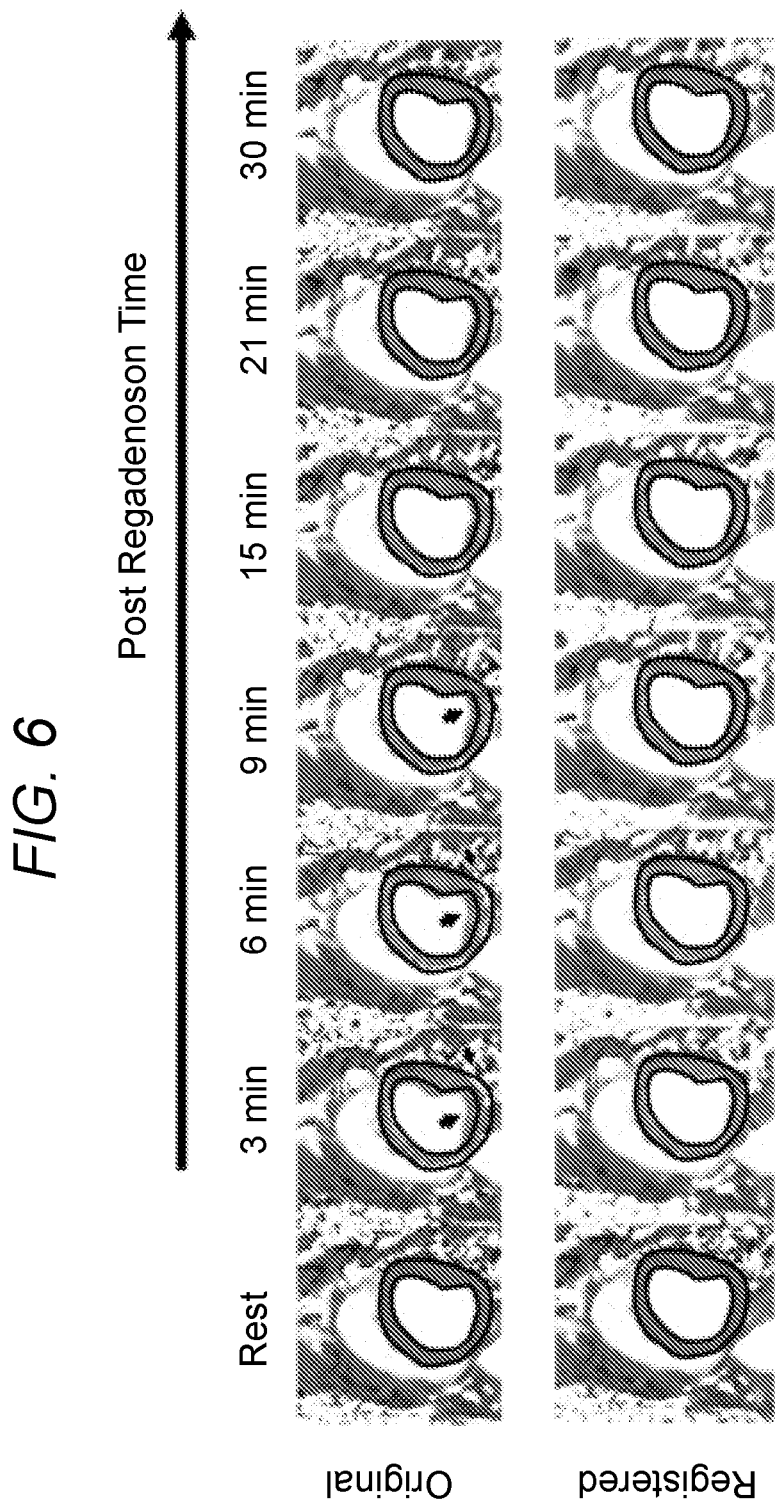
FIG. 6 illustrates, in accordance with various embodiments of the invention, the effect of the non-rigid motion correction algorithm. Contour mismatch (black arrows) from the original images are successfully registered to the rest image after motion correction.

Image Processing: The series of BOLD images acquired post regadenoson administration were aligned using the advanced normalization tools (ANTS software). Rest images were used as the reference for registration. For each subject, ANTS utilized a cross-correlation-based symmetric diffeomorphic transformation between the reference image and the target images to minimize image differences. The representative effect of image registration is presented in FIG. 6.

Aligned images were used to fit CDPs on a pixel-by-pixel basis in the myocardial ROI. In all studies, a mono exponential model $T_2(t)=T_{2o} \pm \Delta T_{2max} \exp(-t/\tau)$ (Felmlee M A, Morris M E, Mager D E. Mechanism-based pharmacodynamic modeling. Methods in molecular biology 2012; 929: 583-600) was used to represent the BOLD signal modulation post regadenoson injection and extract CDP maps from BOLD images of the whole period ($T_{2o}$=baseline $T_2$, ms; $\Delta T_{2max}$=Maximum BOLD stimulation amplitude, ms; coronary relaxation time constant, min). The rest images were set to be the fully decayed to baseline BOLD signal at 2 hours after regadenoson injection in the dynamic curve fitting (Gordi T, Frohna P, Sun H L, Wolff A, Belardinelli L, Lieu H. A population pharmacokinetic/pharmacodynamic analysis of regadenoson, an adenosine A2A-receptor agonist, in healthy male volunteers. Clinical pharmacokinetics 2006; 45:1201-12) In the diseased animal, CDPs were fitted with different starting time points (2 mins, 5 mins and 10 mins) to investigate the influence decreased sampling of data points close to the peak vasodilation.

Figure 7:
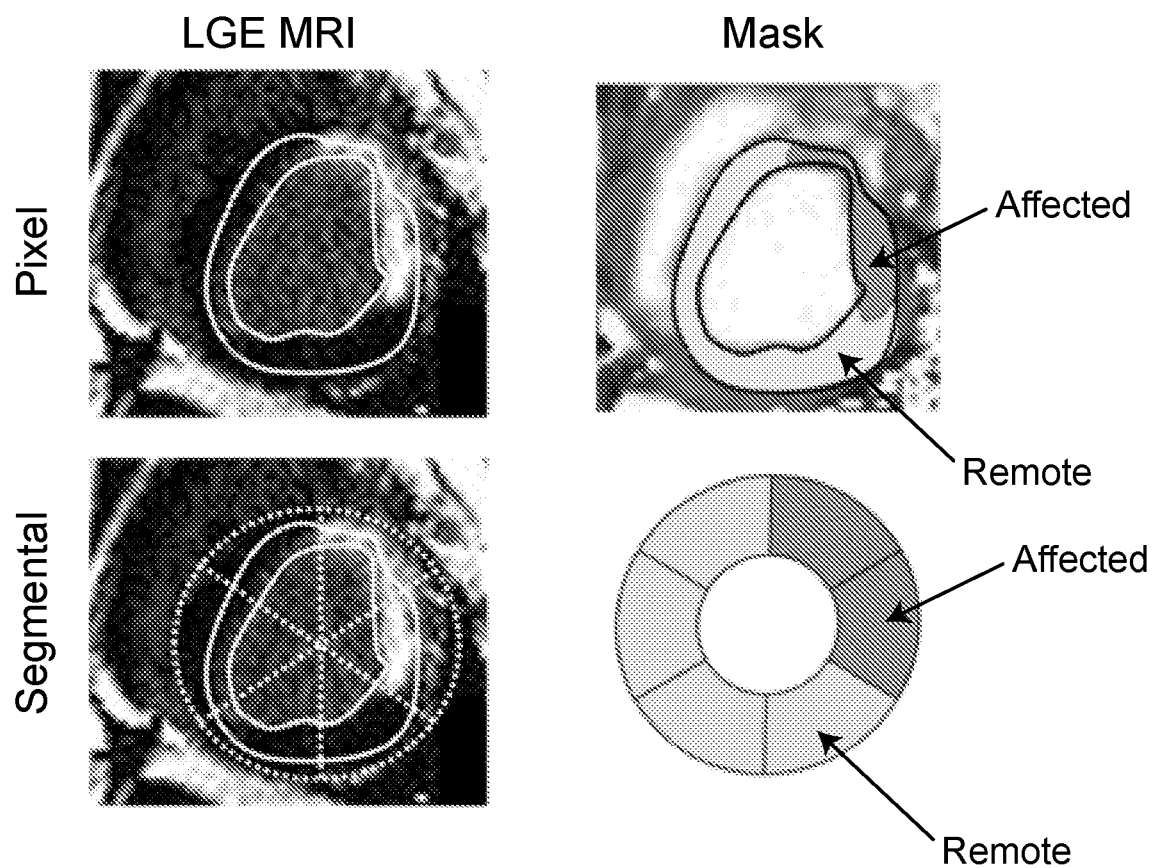
FIG. 7 illustrates, in accordance with various embodiments of the invention, infarcted territories identified from Late Gadolinium Enhancement (LGE) images. Pixel-wise and segmental masks of infarcted territories identified with +5 SD standard are presented. Remote territories are labeled with light gray and affected territories are labeled with dark gray.

Image analysis: In the studies performed in healthy volunteers and animals, global myocardial CDPs were extracted to investigate the feasibility of probing BOLD response. Myocardium was segmented with epi- and endocardial contours. Global myocardial CDPs were measured and compared with the conventional single time point T2 response between Rest and Stress. In the studies with coronary impairment, infarcted territories were identified using LGE images with remote +5 SD criteria (FIG. 7).

Figure 8:
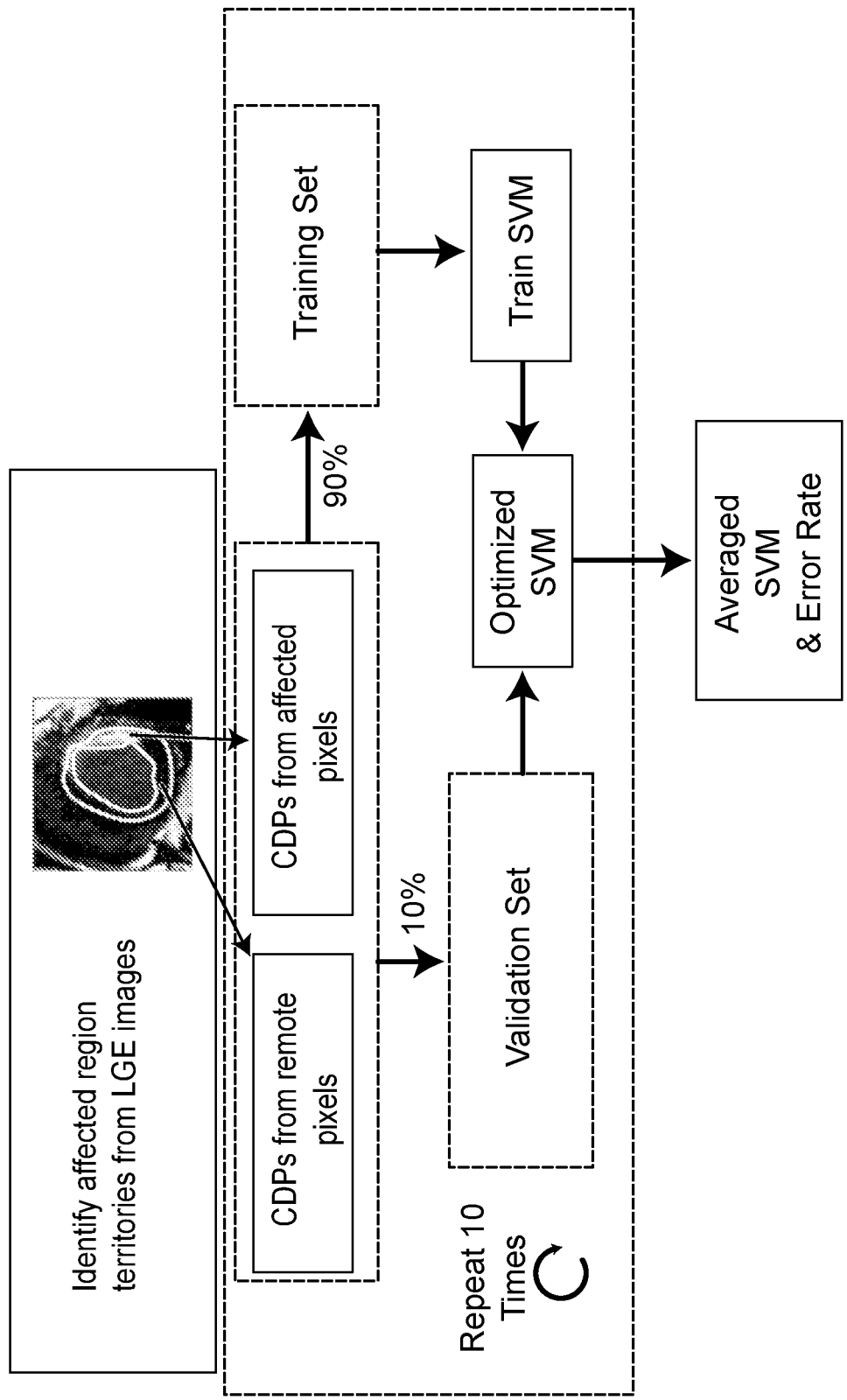
FIG. 8 illustrates, in accordance with various embodiments of the invention, a flow chart of the Support Vector Machine (SVM) cross validation process for evaluating the disease separation capability of the Coronary Dynamic Parameters (CDP's). The myocardial pixels were labeled using Late Gadolinium Enhancement (LGE) images before the SVM training. Myocardial CDP's are separated into 10 subgroups in which 9 groups will be used to train a SVM. The SVM is used to segment the last group to test the segmentation accuracy and examine the disease identification capability from the CDP's. The process is repeated for 10 times to cross validate the whole dataset.

The capability of identifying the affected myocardium on the CDPs was examined using cross validation of support vector machines (SVMs) (FIG. 8) and compared with the conventional single time point T2 based classification. The analysis was first performed in a pixel-wised fashion and compared on the basis of standard AHA segmentation (FIG. 7).

In addition, simultaneously acquired quantitative PET images were used to derive myocardial perfusion reserve (MPR) with a clinical validated software (QPET, Cedars-Sinai Medical Center, Los Angeles) and to validate the reduced MPR in the infarcted myocardium.

Coronary Dynamics in Health. A representative set of temporal resolved BOLD signal and the fitted CDP curve from a healthy human subject and an intact dog is presented in FIG. 9. Representative data showed high Pearson correlation (R) values to the exponential fit (Human: R=0.97, Dog: R=0.93). Fitted CDPs of the healthy studies are presented in Table 1.

TABLE 1

| Parameters | $T_{2o}$ (ms) | $\Delta T_{2max}$ (ms) | $\tau$ (min) | R | $MBR_{CDP}$ (%) | $MBR_{con}$ (%) |
|---|---|---|---|---|---|---|
| Dogs | 34.6 ± 2.1 | 8.6 ± 3.6 | 38.5 ± 28.0 | 0.97 ± 0.06 | 25.8 ± 9.2 | 10.1 ± 3.4 |
| Human | 44.2 ± 6.7 | 14.7 ± 5.8 | 35.6 ± 28.8 | 0.92 ± 0.02 | 26.5 ± 16.1 | 12.0 ± 5.4 |

Figure 10:
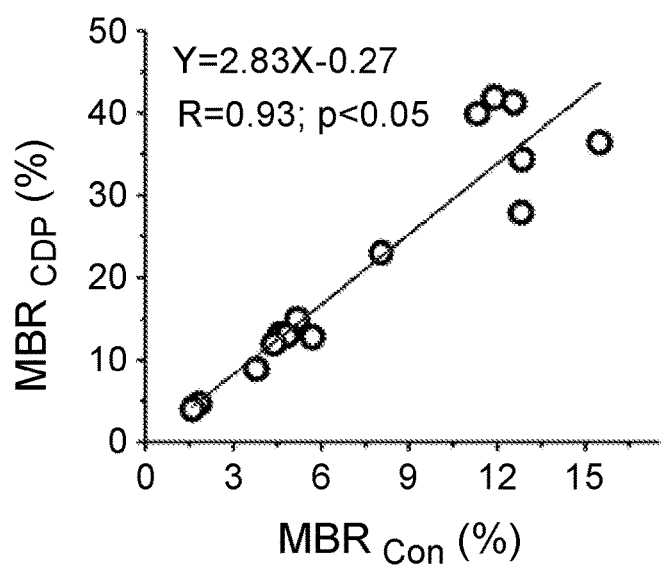
FIG. 10 illustrates, in accordance with various embodiments of the invention, linear regression between $MBR_{CDP}$ and $MBR_{con}$. The regression shows $MBR_{CDP}$ is significantly correlated with the conventional $MBR_{con}$, but the $MBR_{CDP}$ shows significantly larger amplitude compared to $MBR_{con}$.

High R-values demonstrated the model is suitable to reports on the dynamics of the BOLD signal. CDPs are comparable between human and dogs and are in reasonable physiological ranges (Giri S, Chung Y C, Merchant A et al. T2 quantification for improved detection of myocardial edema. Journal of cardiovascular magnetic resonance: official journal of the Society for Cardiovascular Magnetic Resonance 2009; 11:56; Gordi T, Frohna P, Sun H L, Wolff A, Belardinelli L, Lieu H. A population pharmacokinetic/pharmacodynamic analysis of regadenoson, an adenosine A2A-receptor agonist, in healthy male volunteers. Clinical pharmacokinetics 2006; 45:1201-12). In addition, the mean $MBR_{CDP}$ ($\Delta T_{2max}/T_{2o} \times 100\%$) was significantly larger than the mean $MBR_{con}$, which indicates the recovered (magnified) BOLD sensitivity from the CDP extraction. The $MBR_{CDP}$ correlated with the conventional single time point MBR with a linear regression model is shown in FIG. 10.

The $MBR_{CDP}$ was strongly correlated with $MBR_{con}$ (R=0.93; p<0.05). The regression also shows a slope significantly larger than 1 (Y=2.83X−0.27), which indicates the increased BOLD sensitivity with the extracted CDPs compared to the conventional approach.

Figure 11:
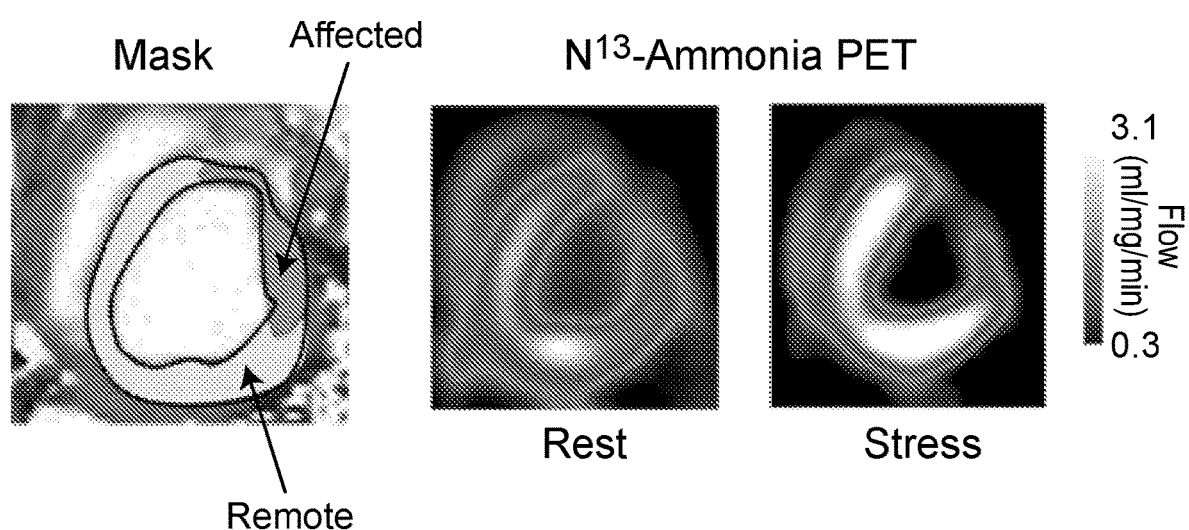
FIG. 11 illustrates, in accordance with various embodiments of the invention, a mask of the infarcted territory identified by Late Gadolinium Enhancement (LGE) (dark gray) and the corresponding $^{13}$N-ammonia PET images. Excellent agreement between the infarcted territories and the perfusion deficit shows the reduced blood supply in the affected myocardium.
Figure 12:
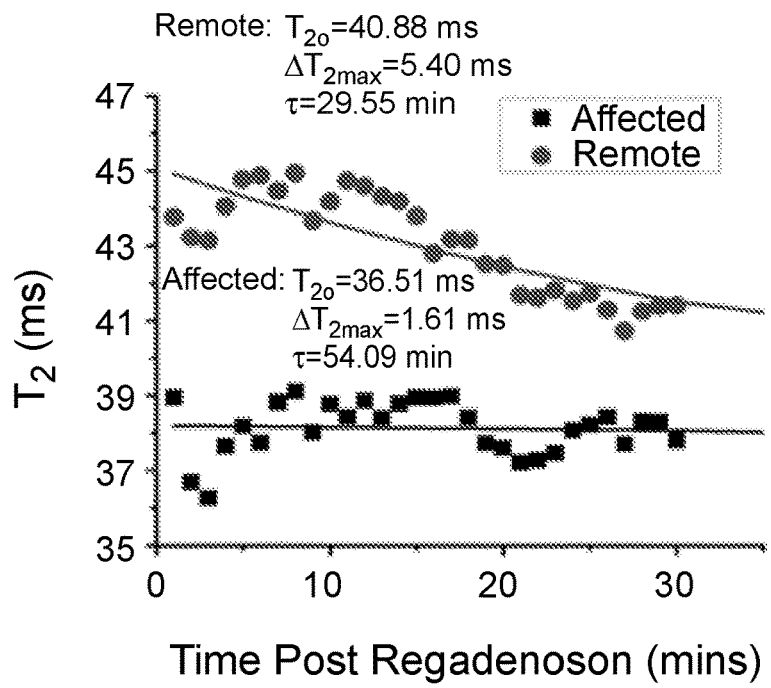
FIG. 12 illustrates, in accordance with various embodiments of the invention, representative BOLD signal dynamics curves extracted from the infarcted animal. Fitted curves are significantly different from remote and affected regions. Obvious reduction on $\Delta T_{2max}$ in the affected curve reflected the reduced perfusion reserve in the infarcted territory.

Coronary Dynamics in an Animal with Myocardial Infarction. The masks of infarcted territories are first compared with $^{13}$N-Ammonia PET to validate the perfusion deficit in the affected region. FIG. 11 presents strong spatial correspondence between infarcted territories from LGE and perfusion deficit from $^{13}$N-Ammonia PET images. Both rest and stress myocardial blood flow were significantly reduced in the affected region and significant lower myocardial perfusion reserve was derived in the infarcted territories (MPR=1.9) compared to the remote myocardium (MPR=3.7). BOLD signal from the remote and affected regions were separated using the affected mask and fitted with the CDP model. The BOLD signal dynamic curve correspond to the remote and affected myocardium are presented in FIG. 12.

Remote and affected area showed significant differences in BOLD signal dynamics, particularly in the maximum $T_2$ response ($\Delta T_{2max}$) and coronary relaxation time constant ($\tau$) (Remote: $\Delta T_{2max}$=5.4 ms, $\tau$=29.6 min vs. affected: $\Delta T_{2max}$=1.6 ms, $\tau$=54.09 min). Significantly lower maximal amplitude of vasodilation and longer relaxation time in the affected region demonstrated the abnormal coronary dynamics in the infarcted region.

CDPs were fitted with different starting time points to assess the effect of sampling after peak vasodilation and to optimize the capability to accurately assess disease. Representative curves fitted from 2, 5 and 10 minutes post-regadenoson injection are presented in FIG. 13.

Figure 13:
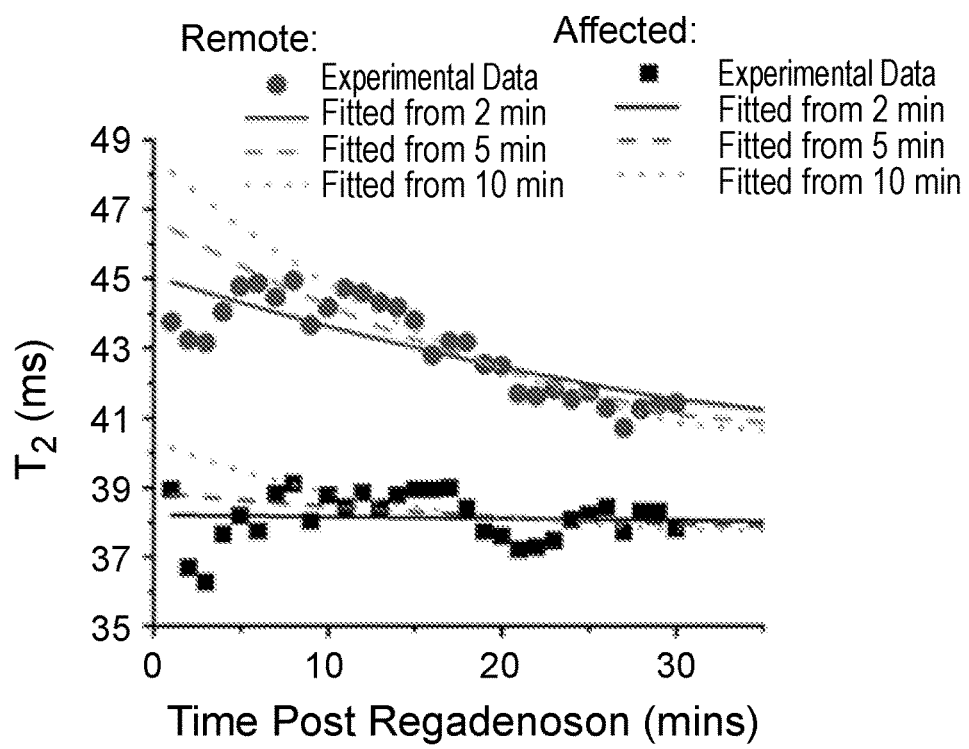
FIG. 13 illustrates, in accordance with various embodiments of the invention, representative Coronary Dynamic Parameter (CDP) curves fitted from different starting time points. Curves were fitted from BOLD sampled from remote (circle) and affected (square) territories. The measured data are represented in circle and square data points and the fitted data are presented in lines.
Figure 14A:
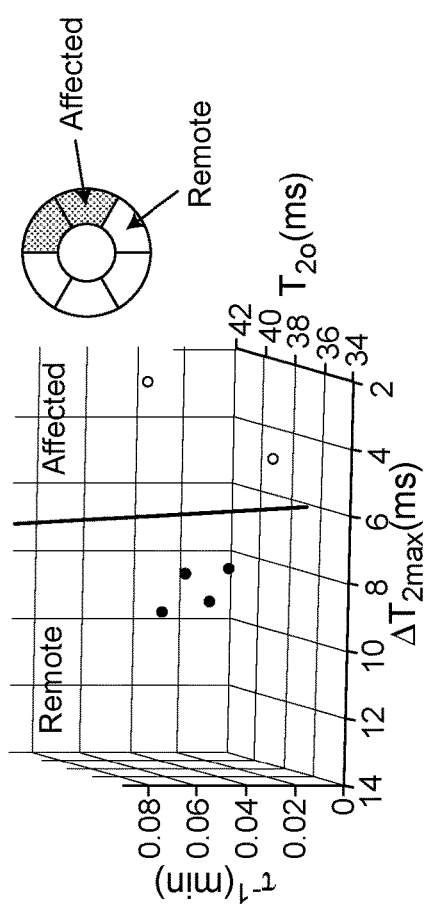
FIG. 14A-FIG. 14D illustrate, in accordance with various embodiments of the invention, segmental evaluation of the remote and affected territories. Coronary Dynamic Parameters (CDPs) derived from different starting time points are plotted in the scatter plots FIG. 14A-FIG. 14C and labeled as remote (black circles) and affected segments (unfilled circles). Infarcted segments were successfully identified from all CDPs and $T_2$ values. Larger margins from the derived Support Vector Machine (SVM) are shown in CDPs from 2 and 5 minutes compared to the 10 minutes and the conventional single time point approach.
Figure 14B:
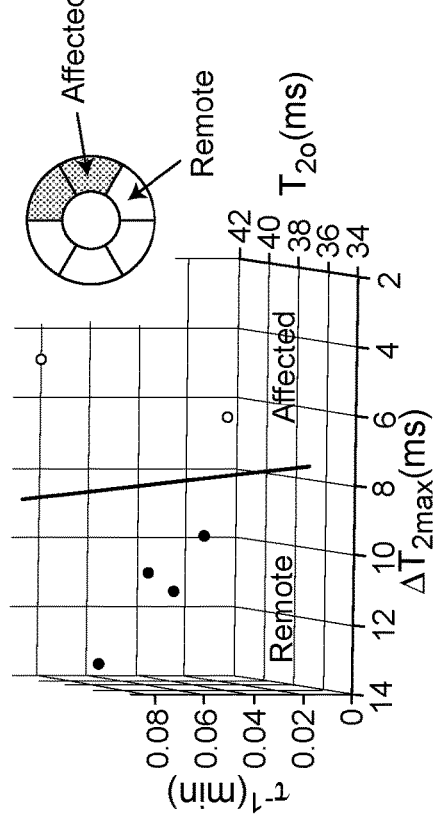
Figure 14D:
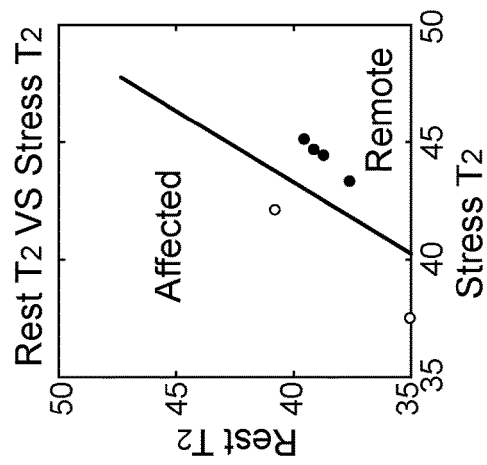
Figure 14C:
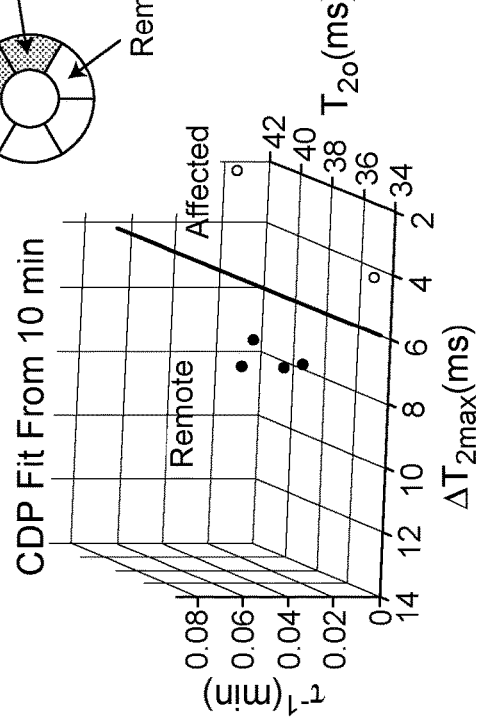
Figure 15B:
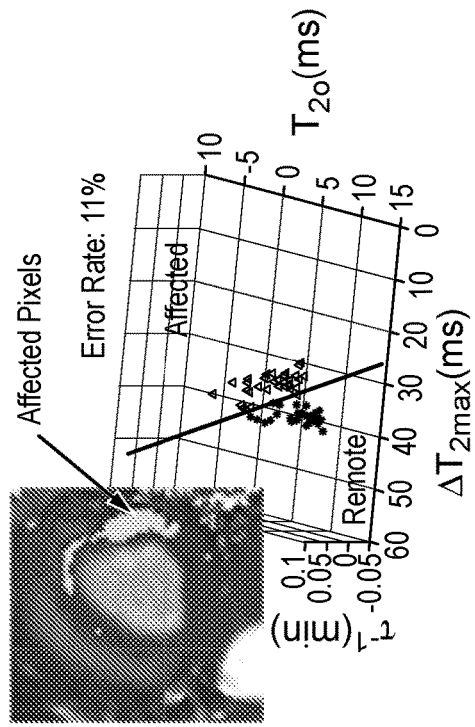
FIG. 15A-FIG. 15D illustrate, in accordance with various embodiments of the invention, pixel-wised evaluation of the remote and affected myocardium. Coronary Dynamic Parameters (CDPs) derived from different starting time points
Figure 15A:
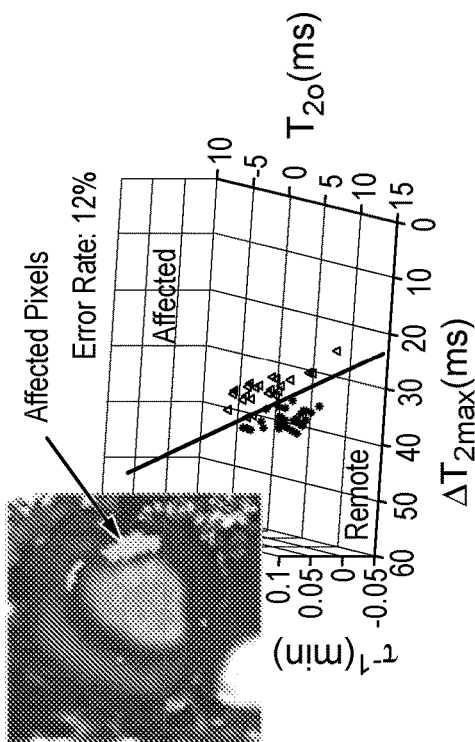
Figure 15D:
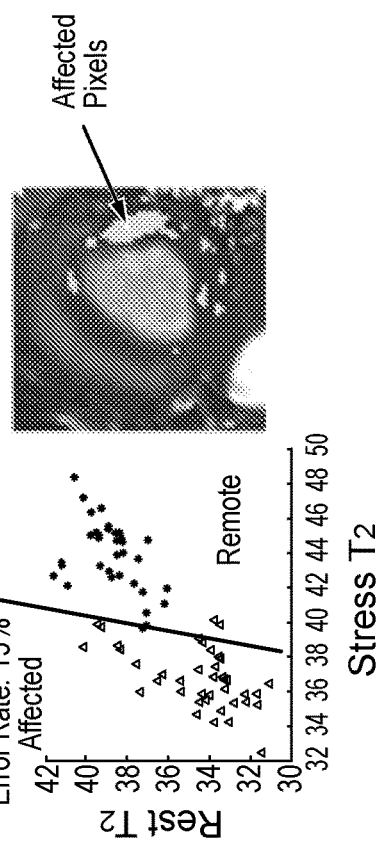
Figure 15C:
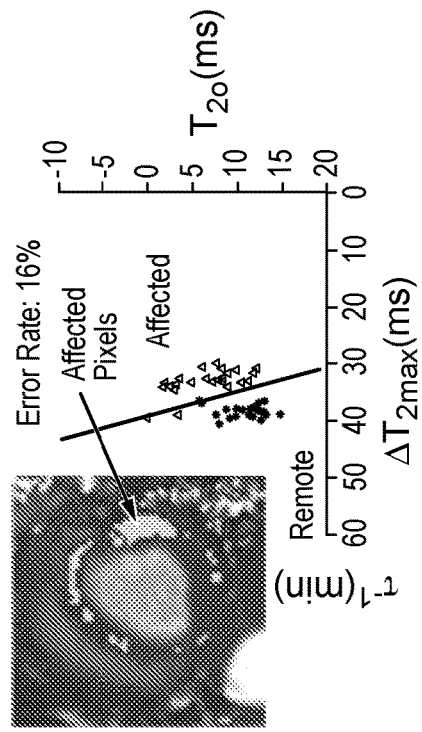
Figure 16A:
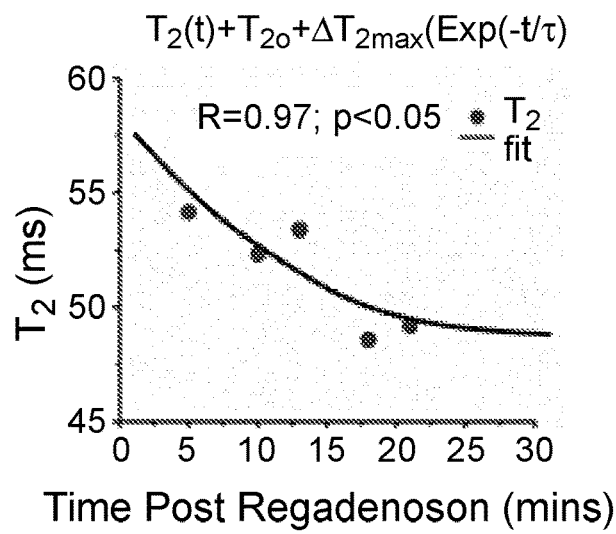
FIG. 16A-FIG. 16C illustrate, in accordance with various embodiments of the invention, that Coronary Relaxation Modeling (CRM) leads to marked improvement in BOLD sensitivity in intact dogs.
Figure 16B:
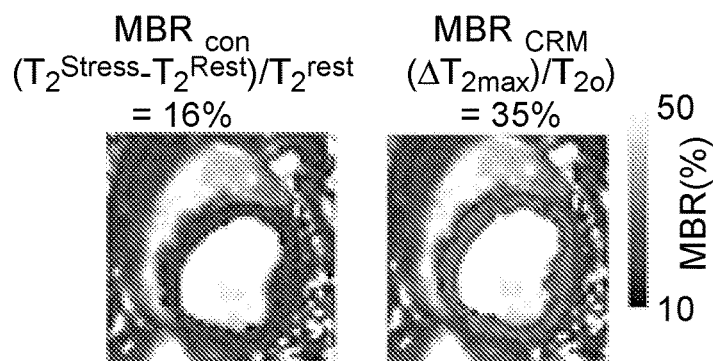
Figure 16C:
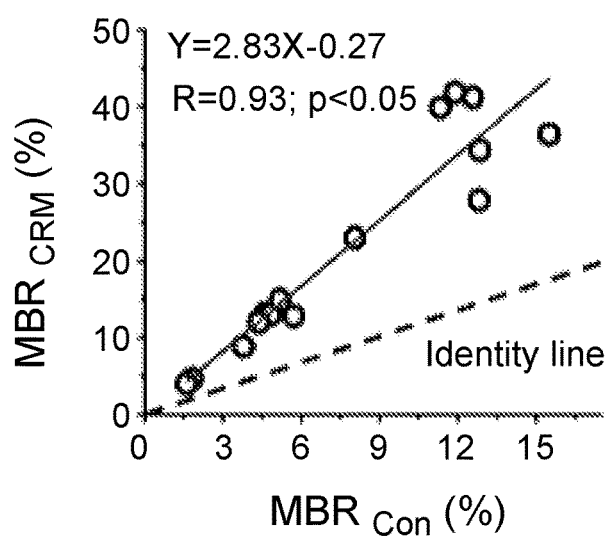
Figure 17A:
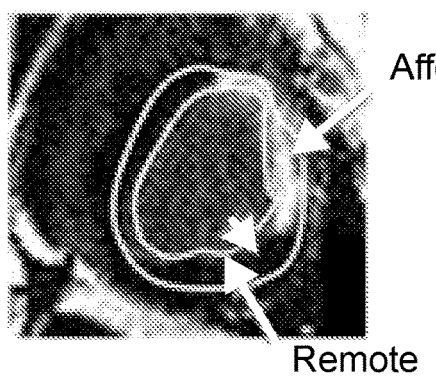
FIG. 17A-FIG. 17D illustrate, in accordance with various embodiments of the invention, Coronary Relaxation Modeling (CRM) for increasing the detection sensitivity of perfusion defect territories with BOLD Cardiovascular Magnetic Resonance (BOLD CMR)
Figure 17B:
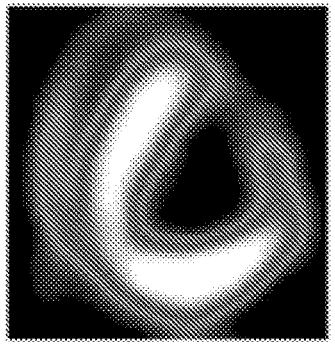
Figure 17C:
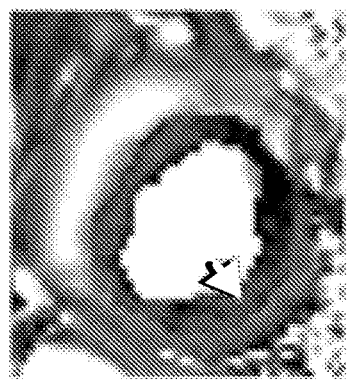
Figure 17D:
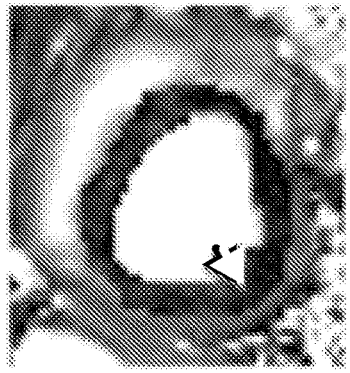

FIG. 13 shows the fitted curves with different starting time points. While the curves shifted among different fitting conditions, the remote and affected curves were clearly separated in all fitted curves. The capability of the derived CDPs in separating the affected and remote myocardium was evaluated in segmental (FIG. 14) and pixel-wise (FIG. 15) fashion. The linear supporting vectors were presented in the CDP scatter plots (FIG. 14 A-FIG. 14C and FIG. 15A-FIG. 15C) to investigate the separability of the parameters and compared with the conventional single time point T2 values (FIG. 14D and FIG. 15D).

FIG. 14 shows the segmental CDPs from an infarcted dog. CDPs fitted from starting 2 min (FIG. 14A), 5 min (FIG. 14B) and 10 min (FIG. 14C) post regadenoson administration are plotted with scatter plot and compared with conventional single time point BOLD signal (FIG. 14D). Affected segments identified from each parameter are labeled with polar plots and presented in the corresponding panel. All CDPs and conventional measures show the capability of separating the remote and affected segments. SVMs from each data sets were derived to investigate the separability between remote and affected segments. Post regadenoson measurement after 2 min and 5 min CDPs showed greater margin from SVM compare to the conventional single time point measurements. The effect demonstrated the possible increased sensitivity of disease identification with multiple measurement and coronary physiological information from the whole vasodilation period.

Pixel-wise analysis from the same animal are presented in FIG. 15. Pixels from remote and affected area are clustered within each group in all CDP scatter plots. Averaged SVMs trained with 10-fold cross validation are presented in the plots and classification error rates were measured to assess the capability of classifying the affected pixels. The affected pixels detected by the averaged SVMs are also presented and labeled in FIG. 15A-FIG. 15D. CDPs fitted from 2 minutes (FIG. 15A) and 5 minutes (FIG. 15B) post regadenoson showed higher accuracy compared to the conventional method (FIG. 15D) while 10 minute (FIG. 15C) CDPs presented slightly lower measures. Among all measurements, 5 mins CDPs showed the best classification property and lowest error rates in both segmental and pixel-wise analysis.

In this study, coronary dynamics following regadenoson injection was assessed in dogs and humans with repeatedly acquired BOLD CMR. In healthy subjects, CDPs were extracted and the fitted parameters were closely correlated to the conventional single time point BOLD response. Maximum BOLD response extracted from CDPs showed the possible increased BOLD sensitivity relative to the conventional single time point MBR calculation. In the infracted dog, CDPs derived from 5 minutes post regadenoson showed the maximum capacity for classifying remote and affected myocardium in both segmental and pixel-wise analysis.

Increased Robustness of BOLD CMR with CDP Estimation. Reliability of BOLD images and the robustness of BOLD response are currently the key barriers for the clinical adoption of BOLD CMR. The capability to repeatedly sample the BOLD signal reduces the susceptibility to imaging and physiological noise compared to the standard single acquisition, which helps increase the robustness of the exams. This is enabled by the capability of regadenoson and is ideally suited for BOLD exam for two reasons: (A) due to the significant heart rate elevation and unstable cardiac motion at the initial phase (3-5 min) (Gordi T, Frohna P, Sun H L, Wolff A, Belardinelli L, Lieu H. A population pharmacokinetic/pharmacodynamic analysis of regadenoson, an adenosine A2A-receptor agonist, in healthy male volunteers. Clinical pharmacokinetics 2006; 45:1201-12) post injection, imaging artifacts can significantly confound the BOLD signals. The capability of bypassing this unpredictable period with repeated measured BOLD CMR is ideal for extracting BOLD signal changes; and (B) The second phase of pharmacological half-life of regadenoson is approximately 30 minutes (Al Jaroudi W, Iskandrian A E. Regadenoson: a new myocardial stress agent. Journal of the American College of Cardiology 2009; 54:1123-30). The time scale is ideal for BOLD CMR acquisitions to sample the coronary activity post-regadenoson administration.

Valued-Added Benefits of Characterizing Coronary Dynamics. In the conventional stress exams, due to the limitation of perfusion imaging methods (typically aimed to capture the first-passage of the contrast agent), coronary reactivity (response) is only evaluated at a single time point (i.e., at peak vasodilation). Notably, the conventional noninvasive perfusion exams, such as SPECT, PET and first pass perfusion MRI, are usually based on imaging contrast agent dynamics. These approaches are not suitable for repeat measurements due to the dose of contrast agent, radiation and contrast washout speed. Although, peak MPR assessed with these methods provide important information in evaluating coronary function, a noninvasive way of determining the complete dynamics of the coronary arteries following regadenoson has the capacity to provide more information. For example, it provides the temporal dimension to study the actual condition of the coronary arteries, which is currently not available. Such a method can offer opportunities to assess time-dependent coronary relaxation and myocardial perfusion in patients experiencing coronary vasospasms.

We used a mono-exponential model as a first-order approximation to model the pharmacodynamics (Felmlee M A, Morris M E, Mager D E. Mechanism-based pharmacodynamic modeling. Methods in molecular biology 2012; 929:583-600) of regadenoson mediating coronary relaxation. The extracted CDPs from the healthy subjects are in accordance with previously reported values (Giri S, Chung Y C, Merchant A et al. $T_2$ quantification for improved detection of myocardial edema. Journal of cardiovascular magnetic resonance: official journal of the Society for Cardiovascular Magnetic Resonance 2009; 11:56; Jaroudi S, Kakourou G, Cawood S et al. Expression profiling of DNA repair genes in human oocytes and blastocysts using microarrays. Human reproduction 2009; 24:2649-55). In the animal with chronic MI, the CDPs were significantly different in the infarcted segments from the normal values. The difference showed the abnormal coronary reactivity in the affected myocardium compared to the remote myocardium to be consistent with the expectation that there would be no or little dynamical response in a regions supplied by a culprit artery that caused an infarction.

The current study showed the mono-exponential fit can capture sufficient differences in CDPs to differentiate remote and infarcted myocardial segments. Furthermore, the repeat measurement strategy can be used to further accelerate the imaging acquisition by exploring the temporal sparsity. While this study fitted the coronary dynamics with a mono-exponential model, additional models (Felmlee M A, Morris M E, Mager D E. Mechanism-based pharmacodynamic modeling. Methods in molecular biology 2012; 929:583-600) may also be used to provide fitting for the BOLD signal dynamics.

Repeatedly acquired BOLD CMR post regadenoson administration enables the extraction of coronary relaxation parameters and capture the BOLD response from peak vasodilation. CDP have the capacity to reliably differentiate disease and healthy myocardium and have better tolerance for degraded image quality, hence improving the reliability of BOLD CMR. Furthermore, repeatedly acquired BOLD CMR post vasodilator administration is a non-contrast and non-radioactive method with the capability of acquiring temporal information of the coronary dynamic and the coronary dynamic parameters, which can provide important insight into the coronary artery and the cardiovascular system. Moreover, repeatedly acquired BOLD CMR post vasodilator administration can fill a critical need for low risk preventative coronary artery disease exams and preventative cardiovascular disease exams.

Example 3

In the past two decades BOLD CMR has seen major advances. Yet, the reliability of BOLD CMR remains a major weakness for its widespread clinical use. A key unresolved obstacle with BOLD CMR is the artifactual signal changes that are typically observed during vasodilator stress. We hypothesized that if BOLD images following vasodilation can be repeatedly acquired, they could be used to improve the reliability of BOLD CMR. We tested our hypothesis by acquiring multiple BOLD images post regadenoson (a coronary vasodilator with the capability to extend vasodilatory state to tens of minutes) injection and estimating the BOLD response parameters with a coronary relaxation model (CRM) based on the pharmacokinetics of regadenoson. We validated our findings with $^{13}N-NH_3$ PET perfusion images.

Intact (n=7) and infarcted (n=2) dogs were studied in a hybrid PET/MR system. 2D BOLD ($T_2$ maps), LGE and $^{13}N-NH_3$ PET images were acquired at rest and at post-regadenoson administration (p.r.a.). $T_2$ maps post-regadenoson administration (p.r.a.) were repeatedly acquired over 30 mins and were registered to $T_2$ maps at rest. These time-dependent $T_2$ maps were then used to model the coronary relaxation as $T_2(t)=T_{2o}+\Delta T_{2max} \exp(-t/\tau)$, where $T_{2o}$, $\Delta T_{2max}$ and $\tau$ are fit parameters with $T_{2o}=T_2$ at rest; $\Delta T_{2max}$=maximal $T_2$ change from rest; and $\tau$=time constant of coronary relaxation. Maximum BOLD response from CRM was estimated ($MBR_{CRM}=\Delta T_{2max}/T_{2o}\times 100\%$) and compared to conventional myocardial BOLD response [$MBR_{con}=(T_2^{2min}-Rest\ T_2)/Rest\ T_2\times 100\%$, where $T_2^{2min}$=myocardial $T_2$ at 2 min p.r.a and Rest $T_2=T_2$ prior to regadenoson injection] using a regression model. In infarcted dogs, affected zones were identified using Late Gadolinium Enhancement (LGE). BOLD contrast-to-noise ratio (CNR) between remote and affected zones (CNR= ($\mu MBR_{Remote}-\mu MBR_{Affected})/\sigma MBR_{Remote}$, where $\mu$ and $\sigma$ are the mean and std dev) were estimated for $MBR_{CRM}$ and $MBR_{con}$ and compared. MBRs were validated with perfusion reserve from PET myocardial perfusion reserve (MPR).

In intact dogs, myocardial $T_2$ dynamics was nicely fitted with CRM (R=0.92±0.06). Parameters estimated from CRM ($T_{2o}$:44.2±6.7 ms; $\Delta T_{2max}$:14.7±5.8 ms; $\tau$:35.5±26.8 min)

were in agreement with previous reports. Both MBRs ($MBR_{CRM}$=27±16% and $MBR_{con}$=12±6%) were consistent with p.r.a PET (MPR=3.0±0.6). $MBR_{CRM}$ and $MBR_{con}$ were highly correlated (R=0.93; p<0.05) with $MBR_{CRM}$=2.83$MBR_{con}$−0.27, indicating that $MBR_{CRM}$ was ~2.8-fold higher than the $MBR_{con}$. In infarcted dogs, significantly higher MBRs in the remote and lower MBRs in the affected regions were observed with both methods (Remote: $MBR_{CRM}$=27±6%, $MBR_{con}$=15±5%; Affected: $MBR_{CRM}$=1±10%, $MBR_{con}$=5±7%; both p<0.05), and were in agreement with PET ($MPR_{remote}$=3.7±0.6; $MPR_{affected}$=1.9±0.7). Mean CNR based on CRM were nearly 2-fold larger than the conventional approach ($CNR_{CRM}$=3.7±0.6; $CNR_{con}$=1.9±0.7).

Our findings support the hypothesis that that repeatedly acquired BOLD CMR post-regadenoson administration (p.r.a) can be used to significantly improve the reliability limitations of current myocardial BOLD CMR.

To provide aspects of the present disclosure, embodiments may employ any number of programmable processing devices that execute software or stored instructions. Physical processors and/or machines employed by embodiments of the present disclosure for any processing or evaluation may include one or more networked (Internet, cloud, WAN, LAN, satellite, wired or wireless (RF, cellular, WiFi, Bluetooth, etc.)) or non-networked general purpose computer systems, microprocessors, filed programmable gate arrays (FPGAs), digital signal processors (DSPs), micro-controllers, smart devices (e.g., smart phones), computer tablets, handheld computers, and the like, programmed according to the teachings of the exemplary embodiments. In addition, the devices and subsystems of the exemplary embodiments can be implemented by the preparation of application-specific integrated circuits (ASICs) or by interconnecting an appropriate network of conventional component circuits. Thus, the exemplary embodiments are not limited to any specific combination of hardware circuitry and/or software.

Stored on any one or on a combination of computer readable media, the exemplary embodiments of the present disclosure may include software for controlling the devices and subsystems of the exemplary embodiments, for driving the devices and subsystems of the exemplary embodiments, for enabling the devices and subsystems of the exemplary embodiments to interact with a human user, and the like. Such software can include, but is not limited to, device drivers, firmware, operating systems, development tools, applications software, database management software, and the like. Computer code devices of the exemplary embodiments can include any suitable interpretable or executable code mechanism, including but not limited to scripts, interpretable programs, dynamic link libraries (DLLs), Java classes and applets, complete executable programs, and the like. Moreover, processing capabilities may be distributed across multiple processors for better performance, reliability, cost, or other benefits.

Common forms of computer-readable media may include, for example, a floppy disk, a flexible disk, a hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read. Such storage media can also be employed to store other types of data, e.g., data organized in a database, for access, processing, and communication by the processing devices.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

What is claimed is:

1. A blood oxygen level dependent (BOLD) magnetic resonance imaging (MRI) method for obtaining one or more coronary dynamic parameters (CDPs) of a subject's cardiovascular system, comprising:
(a) imaging the subject's cardiovascular system at rest to obtain a rest BOLD image;
(b) administering to the subject an effective amount of a vasodilator for inducing hyperemic response in the subject, wherein the vasodilator induces an extended vasodilatory state in the subject;
(c) obtaining a series of BOLD images of the subject's cardiovascular system at two or more time points following the administration of the vasodilator to obtain a plurality of stress images;
(d) registering each of the plurality of stress images to the rest BOLD image to obtain a plurality of motion-corrected images, thereby obtaining BOLD signals of the two or more time points following the administration of the vasodilator based on the plurality of the motion-corrected images;
(e) fitting the BOLD signals of the two or more time points following the administration of the vasodilator with a first mathematical model;
(f) solving for one or more fixed parameters of the first mathematical model to extract the one or more CDPs; and
(g) identifying a diseased territory of the subject's cardiovascular system based on the one or more extracted CDPs relative to a reference value,
wherein the first mathematical model estimates time-dependent changes of the BOLD signals,
wherein the method improves sensitivity compared to BOLD MRI obtained in single time point acquisitions, and
wherein the BOLD signal comprises a transverse relaxation time and the first mathematical model comprises a mono-exponential model, $T_2(t)=T_{2o}+\Delta T_{2max} \exp(-t/\tau)$, wherein t is a time point following the administration of the vasodilator, $T_2(t)$ is the transverse relaxation time at the t, $T_{2o}$ is a first fixed parameter of the one or more fixed parameters of the mono-exponential model estimating a baseline of the transverse relaxation time, $\Delta T_{2max}$ is a second fixed parameter of the one or more fixed parameters of the mono-exponential model estimating a maximum change in the transverse relaxation time from rest, and $\tau$ is a third fixed parameter of the one or more fixed parameters of the mono-exponential model estimating a coronary constant, and wherein the one or more CDPs comprises the $\Delta T_{2max}$, $\Delta T_{2max}/T_{2o}$, $\Delta T_{2max}/\tau$, or $(\tau \times \Delta T_{2max})$.

2. The method of claim 1, wherein the subject's cardiovascular system comprises the subject's heart.

3. The method of claim 1, wherein the subject's cardiovascular system comprises the subject's coronary arteries.

4. The method of claim 1, wherein the subject's cardiovascular system comprises the subject's myocardium.

5. The method of claim 1, wherein the vasodilator comprises regadenoson, binodenoson, apadenoson, dipyridamole, or adenosine.

6. The method of claim 1, wherein obtaining the series of BOLD images comprises imaging at a time interval, and the time interval is from 1 minute to 30 minutes between each image.

7. The method of claim 1, wherein obtaining the series of BOLD images comprises imaging at a time interval, and the time interval is from 1 minute to 5 minutes between each image.

8. The method of claim 1, wherein obtaining the series of BOLD images comprises imaging at a time interval, and the time interval is from 5 minutes to 10 minutes between each image.

9. The method of claim 1, further comprising applying the one or more extracted CDPs to a second mathematical model to obtain the reference value, wherein a difference in the one or more extracted CDPs relative to the reference value is indicative of a cardiovascular disease in the diseased territory of the subject's cardiovascular system.

10. The method of claim 1, wherein the BOLD signal consists of the transverse relaxation time, and the first mathematical model consists of the mono-exponential model.

11. The method of claim 1, wherein the vasodilator is administered intravascularly, intravenously, intraarterially, or intracoronary.

12. The method of claim 1, wherein the vasodilator is administered as a single bolus.

13. The method of claim 1, wherein no radioactive tracer or contrast agent is administered to the subject.

14. The method of claim 1, wherein the subject is a human.

15. The method of claim 1, wherein the vasodilator is a selective $A_{2A}$ adenosine receptor agonist.

16. The method of claim 1, wherein the vasodilator is administered at 0.01-0.02, 0.02-0.03, 0.03-0.04, 0.04-0.05, 0.05-0.06, 0.06-0.07, 0.07-0.08, 0.08-0.09, 0.09-0.1, 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 5-6, 6-7, 7-8, 8-9, or 9-10 mg, or a combination thereof.

17. The method of claim 1, wherein the vasodilator is administered at 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 5-6, 6-7, 7-8, 8-9, 9-10, 10-20, 20-30, 30-40, 40-50, 50-60, 60-70, 70-80, 80-90, or 90-100 µg/kg body weight, or a combination thereof.

18. The method of claim 1, wherein step (c) is performed 5-6, 6-7, 7-8, 8-9, 9-10, 10-11, 11-12, 13-14, 14-15, 15-16, 16-17, 18-19, 19-20, 20-21, 21-22, 22-23, 23-24, or 24-25 minutes after step (b).

19. The method of claim 1, wherein step (c) is performed 10, 11, 12, 13, 14, or 15 minutes after step (b).

20. The method of claim 5, wherein the vasodilator is regadenoson.

21. The method of claim 9, wherein the cardiovascular disease is selected from infarcted myocardium, coronary artery disease, coronary heart disease, ischemic heart disease, cardiomyopathy, stroke, hypertensive heart disease, heart failure, pulmonary heart disease, ischemic syndrome, coronary microvascular disease, cardiac dysrhythmias, rheumatic heart disease, aortic aneurysms, cardiomyopathy, atrial fibrillation, congenital heart disease, endocarditis, inflammatory heart disease, inflammatory cardiomegaly, myocarditis, valvular heart disease, cerebrovascular disease, and peripheral artery disease.

22. The method of claim 9, wherein the cardiovascular disease is ischemic heart disease.

23. The method of claim 9, wherein the cardiovascular disease is infarcted myocardium.

24. The method of claim 9, wherein the second mathematical model is a Gaussian mixed model (GMM).

25. The method of claim 12, wherein the single bolus comprises 0.01-0.02, 0.02-0.03, 0.03-0.04, 0.04-0.05, 0.05-0.06, 0.06-0.07, 0.07-0.08, 0.08-0.09, 0.09-0.1, 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 5-6, 6-7, 7-8, 8-9, or 9-10 mg of the vasodilator.

26. The method of claim 24, wherein the reference value is obtained from the Gaussian mixed model (GMM) comprising:

(a) obtaining a weighted sum of two component Gaussian densities by applying the one or more extracted CDPs to the equation:

$$p(x|\mu,\sigma) = \Sigma_i w_i g(x|\mu_i,\sigma_i),$$

wherein p is a summed density, x is the one or more extracted CDPs, i is 1 or 2, and g is the component Gaussian densities determined from the equation:

$$g(x|\mu_i,\sigma_i) = \frac{1}{|\sigma_i|^{1/2}} \exp\left\{-\frac{1}{2}(x-\mu_i)'\sigma_i^{-1}(x-\mu_i)\right\},$$

wherein $\mu_i$ is a mean value, $\sigma_i$ is a covariance, and $w_i$ is a mixture weight, wherein the mixture weight satisfy a constraint that $\Sigma_i w_i = 1$; and (b) defining the component Gaussian density with a larger mean value as the reference value, wherein the reference value is a distribution of a normal myocardium.

27. The method of claim 26, wherein a value of less than mean minus 2 standard deviation (mean-2SD) for the one or more extracted CDPs relative to the reference value is indicative of a diseased myocardium in the diseased territory.

28. The method of claim 26, wherein pixels corresponding to the normal myocardium are identified as remote territories.

29. The method of claim 27, wherein pixels corresponding to the diseased myocardium are identified as affected territories.

30. A method for treating a cardiovascular disease in a subject in need thereof, comprising:
(a) identifying the diseased territory of the subject's cardiovascular system according to the method of claim 27; and
(b) administering a therapeutic treatment to the subject identified with the diseased territory so as to treat the cardiovascular disease.

31. The method of claim 30, wherein the therapeutic treatment is coronary revascularization through stenting, coronary bypass grafting, or medical therapy, or combinations thereof.

32. The method of claim 15, wherein the selective $A_{2A}$ adenosine receptor agonist is regadenoson, or a salt of regadenoson.

* * * * *